United States Patent
Park et al.

(10) Patent No.: US 7,078,407 B2
(45) Date of Patent: Jul. 18, 2006

(54) 4-HYDROXYCINNAMAMIDE DERIVATIVES AS ANTIOXIDANTS AND PHARMACEUTICAL COMPOSITIONS CONTAINING THEM

(75) Inventors: No-Sang Park, Daejeon (KR); Young-Sik Jung, Daejeon (KR); Churl-Min Seong, Daejeon (KR); Hee-Jong Lim, Daejeon (KR); Joong-Ho Yoon, Changwon-si (KR); Jae-Yang Kong, Daejeon (KR); Woo-Kyu Park, Cheongju-si (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 212 days.

(21) Appl. No.: 10/302,686

(22) Filed: Nov. 22, 2002

(65) Prior Publication Data

US 2003/0162789 A1    Aug. 28, 2003

(30) Foreign Application Priority Data

Nov. 23, 2001 (KR) ............... 10-2001-0073301
Nov. 23, 2001 (KR) ............... 10-2001-0073307
Jul. 19, 2002 (KR) ............... 10-2002-0042579

(51) Int. Cl.
*A61K 31/495* (2006.01)
*C07D 295/192* (2006.01)
*C07D 295/96* (2006.01)

(52) U.S. Cl. ............... 514/255.01; 514/252.12; 514/252.13; 514/254.01; 514/617; 514/622; 544/372; 544/379; 544/391; 544/401; 564/170

(58) Field of Classification Search ............... 544/379, 544/391, 401; 514/252.13
See application file for complete search history.

(56) References Cited

U.S. PATENT DOCUMENTS 4,178,442 A * 12/1979 Bourgery et al. ........... 540/596
6,335,445 B1 * 1/2002 Chabrier de Lassauniere et al. ........... 544/358

FOREIGN PATENT DOCUMENTS

WO    WO 97/43259    11/1997
WO    98/42696    * 10/1998

OTHER PUBLICATIONS

DeLassauniere et al. Chemical Abstracts, vol. 129 No. 302557 (1998) Abstract for WO98/42696.*
Bebbington, David, et al., 3,5-Disubstituted-4-hydroxyphenyls Linked to 3-Hydroxy-2-methyl-4(1H)-pyridinone: Potent Inhibitors of Lipid Peroxidation and Cell Toxicity, J. Med. Chem. 2000, 43, 2779-2782.
Jarrott, Bevyn, Development of a Novel Arylalkylpiperazine Compound (AM-36) as a Hybrid Neuroprotective Drug, Drug Development Research 46:261-267 (1999).
Rajan, Padinchare, et al., Synthesis and Evaluation of Caffeic Acid Amides as Antioxidants, Bioorganic & Medicinal Chemistry Letters 11 (2001) 215-217.

* cited by examiner

*Primary Examiner*—Emily Bernhardt
(74) *Attorney, Agent, or Firm*—Lucas & Mercanti, LLP

(57) ABSTRACT

The present invention relates to 4-hydroxycinnamamide derivatives as antioxidants and pharmaceutical compositions containing them. More particularly, it relates to 4-hydroxycinnamamide derivatives showing superior antioxidant activity compared to the known antioxidant compounds, their pharmaceutically acceptable salt, and pharmaceutical compositions containing them. It can be usefully used in treating neurodegerative diseases such as aging, cancer, diabetes, ischemic stroke, Parkin's disease, dementia and Huntinton's disease.

2 Claims, No Drawings

4-HYDROXYCINNAMAMIDE DERIVATIVES AS ANTIOXIDANTS AND PHARMACEUTICAL COMPOSITIONS CONTAINING THEM

This patent application claims a benefit of priority from Korean Patent Application No. 2001/73301 filed Nov. 23, 2001, Korean Patent Application No. 2001/73307 filed Nov. 23, 2001 and Korean Patent Application No. 2002/42579 filed Jul. 19, 2002, the contents of each of which is incorporated herein by reference.

FIELD OF THE INVENTION

The present invention relates to 4-hydroxycinnamamide derivatives as antioxidants and pharmaceutical compositions containing them. More particularly, it relates to 4-hydroxycinnamamide derivatives showing superior antioxidant activity compared to the known antioxidant compounds, their pharmaceutically acceptable salt, and pharmaceutical compositions containing them.

BACKGROUND OF THE INVENTION

Oxygen plays an important role in producing ATP by oxidizing nutrients at the mitochondria inside cells. However, inevitably, 2–5% of the oxygen changes into reactive oxygen species such as superoxide radical($.O_2^-$), hydrogen peroxide($H_2O_2$) and hydroxy radical(HO.) that are harmful to human body.

As a protector against reactive oxygen species, antioxidant enzymes such as superoxide dismutase, catalase and peroxidase, and antioxidant substances such as glutathion and coenzyme Q (CoQ) are present in vivo, and such antioxidant substances can also be intake with food. However, under specific circumstances such as ischemia, too much active oxygen is generated, which exceeds the biological protect system capacity to cause oxidative stress. Such active oxygen attacks the biological cell to destroy lipid, protein and RNA, DNA, and inhibits various enzymes to cause cancer, neurodegerative diseases and cardiovascular diseases and aging.

Thus, antioxidants which eliminate active oxygen or inhibit the generation of active oxygen can not only be used as age resisters or anti cancer drugs, but as therapeutics for various neurodegerative diseases such as dementia and ischemic stroke.

More particularly, active oxygen shows a non-selective, non-reversible destructive reaction against cell components such as lipid, protein, sugar and DNA. Hereupon, enzymes that are naturally generated from low density lipoproteins or plasma protect cells from being oxidized. The prevention of lipid peroxidation is a basic reaction for breathing organisms, and thus, organisms undergoing organic respiration have a defense system that defends the organism from ROS generated by the oxidation reaction of respiration and substrate. A little amount of ROS ($.OH$, $.O_2^-$, $H_2O_2$), or even nitric oxide (NO) and peroxinitrite (ONOO) are continuously generated in the process of respiration by receiving both internal and external stimuli. When the ROS level is low, it plays an important role in protecting it from microorganims or in the biochemical processes of the immune system, cell differentiation, and internal signal transduction. However, on the contrary, when the ROS level exceeds the amount that can be managed in vivo, it is biologically damaged and builds up oxidative stress such as dysfunction in metabolism. If such oxidative toxicity is not eliminated, it damages DNA and inhibits the production of proteins such as $Na^+/K^+$ ATPases and glutamate transporter. Further, if lipid peroxidation increases and the activity of antioxidants decreases, the nuclear center of the cell gets attacked and damages the protein, DNA and RNA to display allergy, variability or herpes virus.

Oxidative stress of ROS which causes such damages can be explained by referring to various pathologic symptoms derived at the central nervous system (CNS), and physical processes such as neurodegerative diseases and aging. The reason ROS is especially fatal to neurodegerative diseases is because the metabolic velocity of oxygen is very high in nervous systems, and the antioxidation degree which defends oxidation maintains a low level. Further, since it contains a high level of unsaturated fatty acid and transition metal, it is very sensitive to oxidation stress. Therefore, if ROS production increases and is not eliminated, cell macromolecules are damaged to a large extent. Accordingly, DNA or protein, lipid are damaged to generate structural, functional abnormal phenomenon. Especially, brain lipid damage due to lipid peroxidation causes fatal neurodegerative diseases.

Such neurodegerative diseases can be classified as acute diseases and chronic diseases. Acute neurodegerative diseases include ischemic stroke, subarachnoid hemorrhage, trauma to the brain and spinal cord, and chronic neurodegerative diseases include Alzheimer's disease, Parkinson's disease, and Huntington's disease. Among these, the mortality rate caused by stroke tends to increase every year all over the world, let alone in Korea.

The field wherein the development of therapeutics for ischemic stroke is being researched most actively is the field of glutamate receptor antagonist. Such therapeutics includes N-methyl-D-aspartate receptor antagonist (NMDA), α-amino-3-hydroxy-4-isoxazole propionic acid receptor antagonist (AMPA), γ-aminobutyric acid (GABA), calcium channel blocker and sodium channel blocker. Recently, research on developing ischemic stroke therapeutics using antioxidants is being performed [Barr, P. R.; Flint Beal, M. *Neuroprotection in CNS Diseases*; Marcel Dekker Inc.].

For a long period of time, antioxidants which eliminate substances harmful to human body have been successively used in protecting synthetic materials or food from being oxidized. Recently, research on antioxidants used as neuro-protecting drugs for various diseases such as Parkinson's disease, Alzheimer's diseases, stroke and traumatic injury is being performed. Antioxidants maintain the active oxygen generated during the respiration process in our body to a certain level as stated above, and treat the ROS free radical by the mutual combination system of antioxidants such as antioxidant enzymes (AOEs), endogenous organic compounds including reduced glutathion or GSH, ubiquinone or coenzyme Q, NADPH, melatonine, uric acid, trace minerals including Se, Zn and Mn, and vitamins including vitamin A, C, and E. However, when diseases are caused by the production of excessive amount of ROS due to the trouble in the system, chemically synthesized antioxidants are used in order to solve such problems. As for antioxidants synthesized as above, BHT (tert-butyl-hydroxytoluene), Idebenone or antioxidative substances of Carbozole and Phenazine have already been developed. [Okamoto, K.; Wasazumi, M.; Morimoto, H.; Imada, I. *Chem. Pharm. Bull.* 1988, 36, 178. Yamaguchi, T.; Sano, K.; Takakura, K.; Saito, I.; Shinohara, Y.; Asano, T.; Yasuhara, H. *Stroke* 1998, 29, 12. Dirnagl. U.; Iadecola, C.; Moskowitz, M. A. *TINS* 1999, 22, 391.].

SUMMARY OF THE INVENTION

It is an object of the present invention to provide 4-hydroxycinnamamide derivatives as antioxidants and pharmaceutical compositions containing them used to prevent aging, to treat cancer, diabetes and fasciola hepatica, and neurodegerative diseases.

DETAILED DESCRIPTIONS OF THE PREFERRED EMBODIMENTS

The present invention provides 4-hydroxycinnamamide derivatives represented by following formula 1 or formula 2, and their pharmaceutically acceptable salts:

FORMULA 1

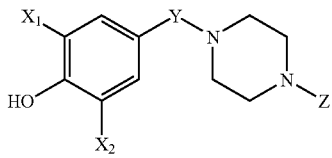

wherein,
$X_1$ and $X_2$ are independently, hydrogen, hydroxy, $C_1$–$C_{15}$ alkyl group or $C_1$–$C_{15}$ alkoxy group;
Y is $C_1$–$C_3$ alkyl group, —CH=CH—C(=O)— or —CH$_2$CH$_2$C(=O)—;
Z is

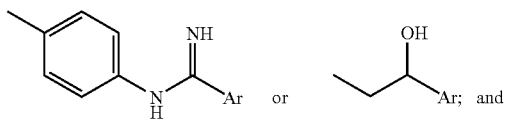

Ar represents phenyl, thiophene or pyrrole group wherein Ar does not contain substituents or contains $C_1$–$C_3$ alkyl, alkoxy, halogen or amino group.

FORMULA 2

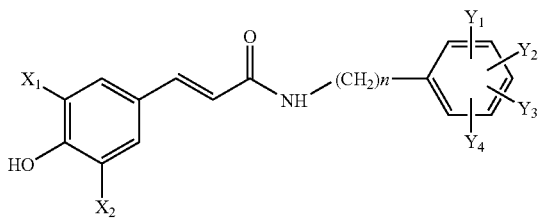

wherein,
$X_1$ and $X_2$ are independently, hydrogen, hydroxy, $C_1$–$C_{15}$ alkyl group or $C_1$–$C_{15}$ alkoxy group;
$Y_1$, $Y_2$, $Y_3$ and $Y_4$ are independently, hydrogen, halogen, hydroxy group, amino group, phenyl group, $C_1$–$C_8$ alkyl group or $C_1$–$C_8$ alkoxy group;
n is an integer of 0 to 9.

More preferable compounds in accordance with the present invention are as follows;

(1) 4-{4-[2-(4-fluorophenyl)-2-hydroethyl]piperazine-1-ylmethyl-2,6-bis-pentyloxyphenol, (2) 4-{4-[2-(4-chlorophenyl)-2-hydroethyl]piperazine-1-ylmethyl}-2,6-bis-nonyloxyphenol, (3) 1-{4-[2-(4-chlorophenyl)-2-hydroethyl]piperazine-1-yl}-3-(4-hydroxy-3,5-dimethoxyphenyl)propenone, (4) 1-{4-[2-(4-chlorophenyl)-2-hydroxyethyl]piperazine-1-yl}-3-(3,5-dibutoxy-4-hydroxyphenyl)propenone, (5) 3-(3,5-dibutoxy-4-hydroxyphenyl)-1-{4-[2-(4-fluorophenyl)-2-hydroxyethyl]piperazine-1-yl}propenone, (6) 3-(3,5-dibutoxy-4-hydroxyphenyl)-1-[4-(2-hydroxy-2-p-toylethyl)piperazine-1-yl]propenone, (7) 3-(3,5-dibutoxy-4-hydroxyphenyl)-1-{4-[2-hydroxy-2-(4-methoxyphenyl)ethyl]piperazine-1-yl}propenone, (8) 3-(3,5-dibutoxy-4-hydroxyphenyl)-1-{4-[2-hydroxy-2-(3-methoxyphenyl)ethyl]piperazine-1-yl}propenone, (9) 1-[4-(2-biphenyl-4-yl-2-hydroxyethyl)piperazine-1-yl]-3-(3,5-dibutoxy-4-hydroxyphenyl)propenone,

(10) 3-(3,5-bis-hexyloxy-4-hydroxyphenyl)-1-{4-[2-(4-fluorophenyl)-2-hydroxyethyl]piperazine-1-yl}propenone,

(11) 3-[3,5-bis-(1-ethylpropoxy)-4-hydroxyphenyl]-1-(4-[2-(4-chlorophenyl)-2-hydroxyethyl]piperazine-1-yl}propenone,

(12) 1-{4-[2-(4-fluorophenyl)-2-hydroxyethyl]piperazine-1-yl}-3-[4-hydroxy-3,5-bis-nonyloxyphenyl]propenone,

(13) 3-(4-hydroxy-3,5-bis-nonyloxyphenyl)-1-[4-(2-hydroxy-2-p-toylethyl)piperazine-1-yl]propenone,

(14) 3-(4-hydroxy-3,5-bis-nonyloxyphenyl)-1-{4-[2-hydroxy-2-(4-methoxyphenyl)ethyl]piperazine-1-yl}propenone,

(15) 3-(4-hydroxy-3,5-bis-nonyloxyphenyl)-1-{4-[2-hydroxy-2-(3-methoxyphenyl)ethyl]piperazine-1-yl}propenone,

(16) 1-[4-(2-biphenyl-4-yl-2-hydroxyethyl)piperazine-1-yl]-3-(4-hydroxy-3,5-bis-nonyloxyphenyl)propenone,

(17) 1-{4-[2-(4-chlorophenyl)-2-hydroxyethyl]piperazine-1-ly}-3-(3, -5-dibutoxy-4-hydroxyphenyl)propane-1-one.

(18) N-(4-{4-[3-(3,5-di-t-butyl-4-hydroxyphenyl)acryloyl]piperazine-1-yl}phenyl)thiophene-2-carboxamidine,

(19) N-(4-{4-[3-(4-hydroxy-3,5-dimethoxyphenyl)acryloyl]piperazine-1-yl}phenyl)thiophene-2-carboxamidine,

(20) N-[4-(4-{3-[3,5-bis-(1-ethylpropoxy)-4-hydroxyphenyl]acryloyl}piperazine-1-yl-phenyl]thiophene-2-carboxamidine,

(21) N-(4-{4-[3-(4-hydroxy-3,5-dipropoxyphenyl)acryloyl]piperazine-1-yl}phenyl)thiophene-2-carboxamidine,

(22) N-(4-{4-[3-(3,5-dibutoxy-4-hydroxyphenyl)acryloyl]piperazine-1-yl}phenyl)thiophene-2-carboxamidine,

(23) N-(4-{4-[3-(4-hydroxy-3,5-bispentyloxyphenyl)acryloyl]piperazine-1-yl}phenyl)thiophene-2-carboxamidine,

(24) N-(4-{4-[3-(3,5-bis-hexyloxy-4-hydroxyphenyl)acryloyl]piperazine-1-yl}phenyl)thiophene-2-carboxamidine,

(25) N-(4-4-[3-(3,5-bis-heptyloxy-4-hydroxyphenyl)acryloyl]piperazine-1-yl)phenyl)thiophene-2-carboxamidine,

(26) N-(4-{4-[3-(4-hydroxy-3,5-bis-nonyloxyphenyl)acryloyl]piperazine-1-yl}phenyl)thiophene-2-carboxamidine,

(27) N-(4-{4-[3-(3,5-di-t-butyl-4-hydroxyphenyl)acryloyl]piperazine-1-yl}phenyl)-1H-pyrrole-2-carboxamidine,

(28) N-(4-{4-[3-(3,5-dibutoxy-4-hydroxyphenyl)acryloyl]piperazine-1-yl}phenyl)-1H-pyrrole-2-carboxamidine,

(29) N-(4-{4-[3-(4-hydroxy-3,5-bis-pentyloxyphenyl)acryloyl]piperazine-1-yl}phenyl)-1H-pyrrole-2-carboxamidine,

(30) N-(4-{4-[3-(3,5-bis-heptyloxy-4-hydroxyphenyl)acryloyl]piperazine-1-yl}phenyl)-1H-pyrrole-2-carboxamidine,

(31) N-(4-{4-[3-(4-hydroxy-3,5-bis-nonyloxyphenyl)acryloyl]piperazine-1-yl}phenyl)-1H-pyrrole-2-carboxamidine,

(32) N-(4-{4-[3-(3,5-di-t-butyl-4-hydroxyphenyl)acryloyl]piperazine-1-yl}phenyl)thiophene-2-carboxamidine hydrochloride,

(33) N-[4-{4-(3-[3,5-bis-(1-ethylpropoxy)-4-hydroxyphenyl]acryloyl)piperazine-1-yl}phenyl]thiophene-2-carboxamidine hydrochloride,

(34) N-(4-{4-[3-(3,5-dibutoxy-4-hydroxyphenyl)acryloyl]piperazine-1-yl}phenyl)thiophene-2-carboxamidine hydrochloride,

(35) N-(4-{4-[3-(3,5-bis-hexloxy-4-hydroxyphenyl)acryloyl]piperazine-1-yl}phenyl)thiophene-2-carboxamidine hydrochloride,

(36) N-(4-{4-[3-(4-hydroxy-3,5-bis-nonyloxyphenyl)acryloyl]piperazine-1-yl}phenyl)thiophene-2-carboxamidine hydrochloride,

(37) N-(4-{4-(3,5-di-t-butyl-4-hydroxybenzyl)piperazine-1-yl}phenyl)thiophene-2-carboxamidine,

(38) N-(4-{4-[3,5-bis-(1-ethylpropoxy)-4-hydroxybenzyl]piperazine-1-yl}phenyl)thiophene-2-carboxamidine,

(39) N-{4-[4-(3,5-dibutoxy-4-hydroxybenzyl)piperazine-1-yl]phenyl}thiophene-2-carboxamidine,

(40) N-{4-[4-(4-hydroxy-3,5-bis-pentyloxybenzyl)piperazine-1-yl]phenyl}thiophene-2-carboxamidine,

(41) N-{4-[4-(3,5-di-t-butyl-4-hydroxybenzyl)piperazine-1-yl]phenyl}-1H-pyrrole-2-carboxamidine,

(42) N-{4-[4-(3,5-dibutoxy-4-hydroxybenzyl)piperazine-1-yl]phenyl}-1H-pyrrole-2-carboxamidine,

(63) 3-(3,5-dimethoxy-4-hydroxyphenyl)-N-[3-(3,4-dimethylphenyl)propyl]acrylamide,

(64) 3-(3,5-dimethoxy-4-hydroxyphenyl)-N-(3,5-di-t-butyl-4-hydroxybenzyl)acrylamide,

(65) 3-(3,5-dimethoxy-4-hydroxyphenyl)-N-[2-(3,5-di-t-butyl-4-hydroxyphenyl)ethyl]acrylamide,

(66) 3-(3,5-dibutoxy-4-hydroxyphenyl)-N-[2-(3,5-di-t-butyl-4-hydroxyphenyl)ethyl]acrylamide,

(67) 3-(3,5-dibutoxy-4-hydroxyphenyl)-N-[4-(3,5-di-t-butyl-4-hydroxyphenyl)butyl]acrylamide,

(68) 3-[3,5-bis-(1-ethylpropoxy)-4-hydroxyphenyl]-N-phenylacrylamide,

(69) 3-[3,5-bis-(1-ethylpropoxy)-4-hydroxyphenyl]-N-(2-hydroxyphenyl)acrylamide,

(70) 3-[3,5-bis-(1-ethylpropoxy)-4-hydroxyphenyl]-N-(3-hydroxyphenyl)acrylamide,

(71) 3-[3,5-bis-(1-ethylpropoxy)-4-hydroxyphenyl]-N-[3-(3,4-dimethylphenyl)propyl]acrylamide,

(72) 3-[3,5-bis-(1-ethylpropoxy)-4-hydroxyphenyl]-N-(3,5-di-t-butyl-4-hydroxybenzyl)acrylamide,

(73) 3-[3,5-bis-(1-ethylpropoxy)-4-hydroxyphenyl]-N-[2-(3,5-di-t butyl-4-hydroxyphenyl)ethyl]acrylamide,

(74) 3-[3,5-bis-(1-ethylpropoxy)-4-hydroxyphenyl]-N-[3-(3,5-di-t-butyl-4-hydroxyphenyl)propyl]acrylamide,

(75) 3-[3,5-bis-(1-ethylpropoxy)-4-hydroxyphenyl]-N-[4-(3,5-di-t-butyl-4-hydroxyphenyl)butyl]acrylamide,

(76) 3-[4-hydroxy-3,5-bis-(1-methylbutoxy)phenyl]-N-phenylacrylamide,

(77) 3-[4-hydroxy-3,5-bis-(1-methylbutoxy)phenyl]-N-(2-hydroxyphenyl)acrylamide,

(78) 3-[4-hydroxy-3,5-bis-(1-methylbutoxy)phenyl]-N-[3-(3,4-dimethylphenyl)propyl]acrylamide,

(79) 3-[4-hydroxy-3,5-bis-(1-methylbutoxy)phenyl]-N-(3,5-di-t-butyl-4-hydroxybenzyl)acrylamide,

(80) 3-[4-hydroxy-3,5-bis-(1-methylbutoxy)phenyl]-N-[2-(3,5-di-t-butyl-4-hydroxyphenyl)ethyl]acrylamide,

(81) 3-[4-hydroxy-3,5-bis-(1-methylbutoxy)phenyl]-N-[3-(3,5-di-t-butyl-4-hydroxyphenyl)propyl]acrylamide,

(82) 3-[4-hydroxy-3,5-bis-(1-methylbutoxy)phenyl]-N-[4-(3,5-di-t-butyl-4-hydroxyphenyl)butyl]acrylamide,

(83) 3-(3,5-bishexyloxy-4-hydroxyphenyl)-N-phenylacrylamide,

(84) 3-(3,5-bishexyloxy-4-hydroxyphenyl)-N-(2-hydroxyphenyl)acrylamide,

(85) 3-(3,5-bishexyloxy-4-hydroxyphenyl)-N-(3-hydroxyphenyl)acrylamide,

(86) 3-(3,5-bishexyloxy-4-hydroxyphenyl)-N-[3-(3,4-dimethylphenyl)propyl]acrylamide,

(87) 3-(3,5-bishexyloxy-4-hydroxyphenyl)-N-(3,5-di-t-butyl-4-hydroxybenzyl)acrylamide,

(88) 3-(3,5-bishexyloxy-4-hydroxyphenyl)-N-[2-(3,5-di-t-butyl-4-hydroxyphenyl)ethyl]acrylamide,

(89) 3-(3,5-bishexyloxy-4-hydroxyphenyl)-N-[3-(3,5-di-t-butyl-4-hydroxyphenyl)propyl]acrylamide,

(90) 3-(3,5-bishexyloxy-4-hydroxyphenyl)-N-[4-(3,5-di-t-butyl-4-hydroxyphenyl)butyl]acrylamide,

(91) 3-(3,5-bisnonyloxy-4-hydroxyphenyl)-N-[2-(3,5-di-t-butyl-4-hydroxyphenyl)ethyl]acrylamide,

(92) 3-(3,5-bisnonyloxy-4-hydroxyphenyl)-N-[3-(3,5-di-t-butyl-4-hydroxyphenyl)propyl]acrylamide,

(93) 3-(3,5-bisnonyloxy-4-hydroxyphenyl)-N-[4-(3,5-di-t-butyl-4-hydroxyphenyl)butyl]acrylamide.

The present invention not only includes 4-hydroxycinnamamide derivatives represented by the above formula 1 or formula 2, and their pharmaceutically acceptable salts but also includes solvates and hydrates which can be prepared from them.

The compounds represented by formula 1 or formula 2 of the present invention may be utilized in the form of salts, and the acid addition salts prepared by adding pharmaceutically acceptable free acids are useful. Compounds of formula 1 and formula 2 may be changed into a corresponding acid addition salt according to the general field practice. Both inorganic and organic acids may be used as free acids in this case. Among inorganic acids, hydorchloric acid, hydrobromic acid, phosphoric acid, sulfuric acid, sodium hydorgen sulfate, nitric acid and carbonic acid may be used. Among organic acids, formic acid, lactobionic acid, salicylic acid, acetylsalicylic acid, methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycollic acid, gluconic acid, galacturonic acid, glutamic acid, glutaric acid, glucuronic acid, aspartic acid, ascorbic acid or hydro iodic acid may be used.

The compound represented by formula 1 or formula 2 of the present invention can be prepared by using the conventional chemical synthesis method or by being extracted from plants. In the present invention, the method for preparation of the compound is not construed to limit the present invention. However, such methods for preparing the compound are not construed to limit the present invention.

More particularly, the preparation method of formula 1 varies according to the Y group.

1. Y is $C_1$–$C_3$ alkyl.

The present invention provides a process for preparing 4-hydroxycinnamamide derivatives (formula 1-1) represented by chemical scheme 1 as follows:

CHEMICAL SCHEME 1

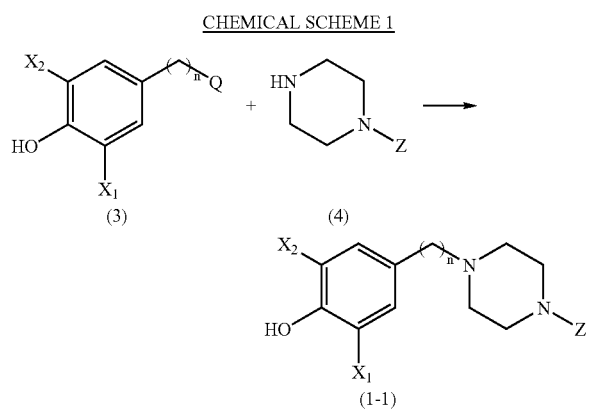

wherein,

Q is halogen, hydroxy or methanesulfonate group; (Q is hydroxy group, halogen or methanesulfonate)

Z is

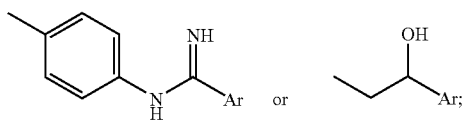

Ar represents phenyl, thiophene or pyrrole group wherein Ar does not contain substituents or contains $C_1$–$C_3$ alkyl, alkoxy, halogen or amino group, n is an integer of 1 to 3.

The process for preparing 4-hydroxycinnamamide derivatives (formula 1-1), wherein Y is $C_1$–$C_3$ alkyl, represented by chemical scheme 1 comprises the step of reacting the compound of formula 3 with the compound of formula 4 to obtain the compound of formula 1-1 (step 1) and reducing the compound of formula 5 to obtain the compound of formula 6 (step 2).

More particularly, 1) if Q is hydroxy, the compound of formula 1 is prepared using the Mitsunobu reaction. For example, the compound of formula 3 is reacted with $PPh_3$ and diethyl azodicarboxylate, and then the compound of formula 4 is added to obtain the compound of formula 1-1.

(2) If Q is halogen or methanesulfonate, the compound is prepared using either organic base or inorganic base. The organic base can be triethylamine, triisopropylamine or pyridine. The inorganic base can be a conventional inorganic base such as sodiumcarbonate and potasiumcarbonate. The reaction temperature and reaction time can be controlled by halogen and methanesulfonate.

2. Y is —CH=CH—C(=O)—

CHEMICAL SCHEME 2

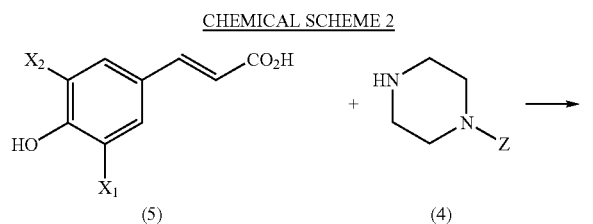

-continued

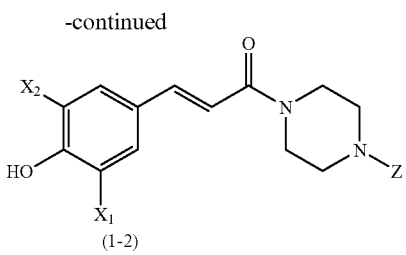

wherein, $X_1$, $X_2$ and Z are as defined in chemical scheme 1.

The process for the compound of formula 1-2, wherein Y is —CH=CH—C(=O)—, represented by chemical scheme 2, comprises the step of reacting the compound formula 5 with the compound of formula 4 to obtain the compound of formula 1-2, wherein Y is —CH=CH—C(=O).

In the step, the compound of formula 5 was reacted with $SOCl_2$, $(COCl)_2$ or $PCl_5$ to obtain an acid chloride compound and the acid chloride compound was reacted with the compound of formula 4 to obtain the compound of formula 1-2. Or the compound of formula 5 was reacted with the compound of formula 4 in the presence of 1,3-dicyclohexylcarbodiimide, 1-(3-dimethylaminopropyl)-3-ethylcarbodiimide hydrochloride, benzotriazol-1-yloxytris(dimethylamino)phosphonium hexafluorophosphate or 1,1'-carbonyldiimidazole to obtain the compound of formula 1-2.

Further, to obtain the compound of formula 1-2, the compound of formula 5 is reacted in the presence of organic metal catalyst or undergoes the conventional carbonyl reduction in the presence of organic metal reagent to obtain the compound of formula 9. NaBH4 is preferable.

The present invention also provides a process for preparing the compound of formula 2, represented by chemical scheme 3 as follows:

CHEMICAL SCHEME 3

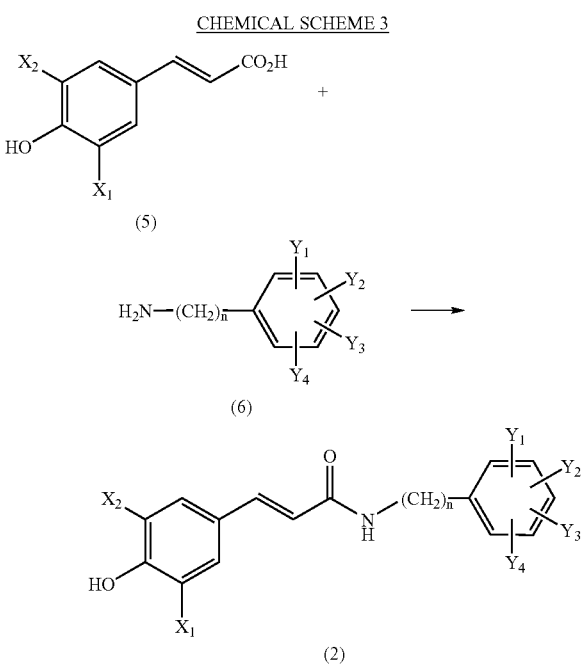

wherein, $X_1$, $X_2$, $Y_1$, $Y_2$, $Y_3$, $Y_4$ and n are as defined in formula 2.

In chemical scheme 3, the compound of formula 5 was reacted with $SOCl_2$, $(COCl)_2$ or $PCl_5$ to obtain an acid chloride and the acid chloride compound was reacted with the compound of formula 6 to obtain the compound of formula 2.

Or the compound of formula 5 was reacted with the compound of formula 6 in the presence of 1,3-dicyclohexylcarbodiimide, 1-(3-dimethylaminopropyl)-3-ethylcarbodiimide hydrochloride, benzotriazol-1-yloxytris(dimethylamino)phosphonium hexafluorophosphate or 1,1'-carbonyldiimidazole to obtain the compoud of formula 2.

Furthermore, the present invention provides pharmaceutical compositions containing 4-hydroxycinnamamides derivatives and its pharmaceutically acceptable salts used to prevent aging, the treat cancer, diabetes and fasciola hepatica, and neurodegerative diseases such as Alzheimer's disease, Parkinson's disease, stroke and Huntington's disease.

4-hydroxycinnamide derivatives of the present invention show antioxidant activity. More particularly, the antioxidation activity level is high when the $IC_{50}$ value is low. As shown in the above table 4, 27% of the antioxidation activity of example 8 increased, 88% of the antioxidation activity of example 12 increased, 56% of the antioxidation activity of example 15 increased and 82% of the antioxidation activity of example 19 and 22 increased compared with the prior antioxidation activator BHT. Thus it can be usefully used in treating neurodegerative diseases such as aging, cancer, diabetes, ischemic stroke, Parkinson's disease, dementia, and Huntington's disease.

That is, the 4-hydroxycinnamide derivatives can be formulated into various dosage forms for oral or parenteral administration. For formulation, pharmaceutically acceptable diluents, expedients and/or carriers may be used, including fillers, thickeners, binders, wetting agents, disintegrants, surfactants, etc. Solid dosage forms for oral administration are exemplified by tablets, pills, powders, granules, and capsules. These solid forms are prepared by admixing neomycine-oxazolidinone heterodimer of formula 1 with at least one expedient, such as starch, calcium carbonate, sucrose, lactose, gelatine, etc. In addition to expedients, lubricants such as magnesium styrate may be added.

Liquid dosage forms for oral administration exemplified by suspensions, internal solutions, emulsions, syrups, etc., may comprise simple diluents, such as water and liquid paraffin, as well as wetting agents, sweeteners, aromatics, and/or perspectives.

Dosage forms for parenteral administration include sterile aqueous solutions, non-aqueous solvents, suspensions, emulsions, freeze-dried agents, suppositories, etc. For formulation of non-aqueous solvents and suspensions, vegetable oils, such as propylene glycol and polyethylene glycol, olive oil or injectable esters such as ethyl oleate, may be used. As basee for syppositories, witepsol, macrogol, Tween 61, cocoa oil, laurinic acid, and glycerogelatine are useful.

The amount of the active ingredient actually administered ought to be determined in light of various relevant factors including the absorptance of active components in vivo, the water active values, the rate of excretion, the age, sex and body of the individual subject, and the severity of the subject's symptoms. In general, the compound of neomycin-oxazolidinone heterodimer may be administrated in a total dose of 0.01–1000 mg per 70 kg a day to adults in 1 or various administrations, preferably, 0.1–500 mg per 70 kg.

A better understanding of the present invention may be obtained in light of the following examples which are set forth to illustrate, but not construed to limit the present invention.

EXAMPLE

Example 1

Preparation of 3-(3,5-dibutoxy-4-hydroxyphenyl)-N-[2-(3,5-di-t-butyl-4-hydroxyphenyl)ethyl]acrylamide To the solution of 3-(3,5-dibutoxy-4-hydroxyphenyl) acrylic acid (130 mg, 0.421 mmol), 4-(2-aminoethyl)-2,6-di-t-butylphenol (110 mg, 0.441 mmol) and HOBT (70 mg, 0.51 mmol) in MeCN 10 ml were DCC at 0° C. After 5 minutes, the solution was stirred for 2 hours at room temperature. And then the precipitate was removed by filtering it through a celite layer and the solution was poured into $CH_2Cl_2$. The solution was washed with 2N HCl and saturated $NaHCO_3$ solution and the water was dried over anhydrous magnesium sulfate and filtered. The obtained filtrate was vacuum concentrated to give the residue, which was purified by column chromatography (EtOAc:Hexane=1:3), yielding 208 mg (91%) of the title compound.

Example 2

Preparation of 3-(3,5-dibutoxy-4-hydroxyphenyl)-N-[4-(3,5-di-t-butyl-4-hydroxyphenyl)butyl]acrylamide To the solution of 3-(3,5-dibutoxy-4-hydroxyphenyl) acrylic acid (53 mg, 0.17 mmol) in DMF (0.76 ml) and $Et_3N$ (39 μl), was added 4-(2-aminoethyl)-2,6-di-t-butylphenol (50 mg, 0.19 mmol) at 0° C. The obtained solution was added with the solution of benzotriazol-1-yloxytris (dimethylamino) phosphonium hexafluorophosphate (84 mg, 0.19 mmol) in $CH_2Cl_2$ (1 ml). The solution was stirred for 30 minutes at 0° C. and then was stirred for 12 hours at room temperature. The solution was added with BOP (70 mg, 0.16 mmol) and was stirred for 1 hour. And then $CH_2Cl_2$ was evaporated in vacuo and the obtained residue was poured into ice water. The residue was extracted with EtOAc and washed with HCl (aq) and $NaHCO_3$ (aq). And then the water was dried over anhydrous magnesium sulfate and filtered. The obtained filtrate was vacuum concentrated to give the residue, which was purified by column chromatography (EtOAc:Hexane=1:2), yielding 51 mg (91%) of the title compound as a brown oil.

Example 3

Preparation of 3-[3,5-bis-(1-ethylpropoxy)-4-hydroxyphenyl]-N-[3-(3,4-dimethylphenyl)propyl] acrylamide To the solution of 3-[3,5-bis-(1-ethylpropoxy)-4-hydroxyphenyl]acrylic acid (20 mg, 0.06 mmol) in DMF (0.2 ml) and $Et_3N$ (10 μl), was added 3(3,4-dimethylphenyl)propylamine (11 mg, 0.07 mmol) at 0° C. and was added the solution of BOP (29 mg, 0.07 mmol) in $CH_2Cl_2$ (0.2 ml). The solution was stirred for 30 minutes at 0° C. And then $CH_2Cl_2$ was evaporated in vacuo and the obtained residue was poured into ice water. The residue was extracted with EtOAc and washed with HCl (aq) and $NaHCO_3$ (aq). And then the water was dried over anhydrous magnesium sulfate and filtered. The obtained filtrate was vacuum concentrated to give the residue, which was purified by column chromatography (EtOAc:Hexane=1:5), yielding 26 mg (90%) of the title compound as a oil.

Example 4

Preparation of 3-[3,5-bis-(1-ethylpropoxy)-4-hydroxyphenyl]-N-(3,5-di-t-butyl-4-hydroxybenzyl)acrylamide To the solution of 3-[3,5-bis-(1-ethylpropoxy)-4-hydroxyphenyl]acrylic acid (30 mg, 0.09 mmol) in DMF (0.2 ml) and $Et_3N$ (10 μl), was added 4-aminomethyl-2,6-di-t-butylphenol (23 mg, 0.10 mmol) at 0° C. and was added the solution of BOP (44 mg, 0.10 mmol) in $CH_2Cl_2$ (0.6 ml). The solution was stirred for 30 minutes at 0° C. and then was stirred for 2 hours at room temperature. And then $CH_2Cl_2$ was evaporated in vacuo and the obtained residue was poured into ice water. The residue was extracted with EtOAc and washed with HCl (aq) and $NaHCO_3$ (aq). And then the water was dried over anhydrous magnesium sulfate and filtered. The obtained filtrate was vacuum concentrated to give the residue, which was purified by column chromatography (EtOAc:Hexane=1:5), yielding 25 mg (50%) of the title compound as a yellow solid.

Example 5

Preparation of 3-[3,5-bis-(1-ethylpropoxy)-4-hydroxyphenyl-N-[4-(3,5-di-t-butyl-4-hydroxyphenyl)butyl]acrylamide To the solution of 3-[3,5-bis-(1-ethylpropoxy)-4-hydroxyphenyl]acrylic acid (30 mg, 0.09 mmol) in DMF (0.6 ml) and Et3N (13 μl) was added 4-(4-aminobutyl-2,6-di-t-butylphenol (28 mg, 0.10 mmol) at 0° C. and was added the solution of BOP (44 mg, 0.10 mmol) in $CH_2Cl_2$ (0.6 ml). The solution was stirred for 30 minutes at 0° C. and then was stirred for 2 hours at room temperature. And then $CH_2Cl_2$ was evaporated in vacuo and the obtained residue was poured into ice water. The residue was extracted with EtOAc and washed with HCl (aq) and $NaHCO_3$ (aq). And then the water was dried over anhydrous magnesium sulfate and filtered. The obtained filtrate was vacuum concentrated to give the residue, which was purified by column chromatography (EtOAc:Hexane=1:5), yielding 48 mg (90%) of the title compound as a brown oil.

Example 6

Preparation of 3-(3,5-bishexyloxy-4-hydroxyphenyl)-N-(2-hydroxyphenyl)acrylamide To the solution of 3-(3,5-bishexyloxy-4-hydroxyphenyl)acrylic acid (40 mg, 0.11 mmol) in DMF (1 ml) and $Et_3N$ (17 μl), was added 2-aminophenol (13 mg, 0.12 mmol) at 0° C. and was added the solution of BOP (53 mg, 0.12 mmol) in $CH_2Cl_2$ (0.6 ml). The solution was stirred for 30 minutes at 0° C. and then was stirred for 1.5 hours at room temperature. And then $CH_2Cl_2$ was evaporated in vacuo and the obtained residue was poured into ice water. The residue was extracted with EtOAc and washed with HCl (aq) and $NaHCO_3$ (aq). And then the water was dried over anhydrous magnesium sulfate and filtered. The obtained filtrate was vacuum concentrated to give the residue, which was purified by column chromatography (EtOAc:Hexane=1:5), yielding 17 mg (34%) of the title compound as a white solid.

The table shows the $^1$H-NMR and melting point result of examples 1–6.

TABLE 1

| example | structure | m.p | $^1$H NMR($CDCl_3$) |
|---|---|---|---|
| 1 | 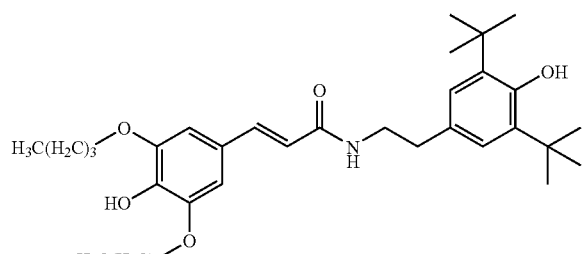 | 82–85° C. | 0.96(t, J=7.4Hz, 6H, 2$CH_3$),1.43(s, 18H, 2C($CH_3$)$_3$), 1.43–1.57(m, 4H, 2$CH_2$), 1.72–1.86(m, 4H, 2$CH_2$), 2.79 (t, J=7.0Hz, 2H, $CH_2$), 3.60(q, J=6.9Hz, 2H, $CH_2$), 4.0 (t, J=6.7Hz, 4H, 2$CH_2$), 5.14(s, 1H, OH), 5.79(br s, 1H, OH), 5.86–5.92(m, 1H, NH), 6.24 (d, J=15.5Hz), 1H, CH=C<u>H</u>CO), 6.71 (s, 2H, ArH), 7.00(s, 2H, ArH), 7.50(d, J=15.5Hz, 1H, C<u>H</u>=CHCO) |
| 2 | 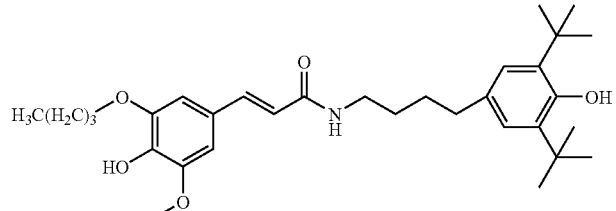 | oil | 0.98 (t, J=7.3Hz. 6H, 2$CH_2$C<u>H</u>$_3$), 1.44(s, 18H, 2C($CH_3$)$_3$), 1.48–1.59(m, 4H, 2C<u>H</u>$_2$CH$_3$), 1.63–1.66 (m, 4H, NHC<u>H$_2$(CH$_2$)$_2$</u>), 1.75–1.88 (m, 4H, 2OCH$_2$C<u>H</u>$_2$), 2.56(t, J=6.8Hz. 2H, NH(CH$_2$)$_3$C<u>H$_2$</u>), 3.34–3.48(m, 2H, NHC<u>H$_2$</u>), 4.05 (t, J=6.5Hz, 4H, 2OCH$_2$), 5.05(s,1H, OH), 5.58(s, 1H, NH), 6.22(d, J=15.3Hz, 1H, COC<u>H</u>=CHAr), 6.71(s, 2H, ArH), 6.97(s, 2H, ArH), 7.49(d, J=15.3Hz, 1H, COCH=C<u>H</u>Ar) |

TABLE 1-continued

| example | structure | m.p | $^1$H NMR(CDCl$_3$) |
|---|---|---|---|
| 3 | (structure: 3,5-bis(diethylmethyleneoxy)-4-hydroxycinnamide with N-propyl-3,4-dimethylphenyl) | oil | 0.97(t, J=7.5Hz, 12H, 4CH$_2$CH$_3$), 1.63–1.79 (m, 8H, 4CH$_2$CH$_3$), 1.80–1.90(m, 2H, NHCH$_2$CH$_2$), 2.22(s, 6H, 2CH$_3$Ar), 2.62(t, J=7.5Hz, 2H, ArCH$_2$CH$_2$), 3.39(q, J=7.1Hz, 2H, CH$_2$NH), 4.09–4.18(m, 2H, 2OCH), 5.60 (br, s, 1H, NH), 5.78(s, 1H, OH), 6.14(d, J=15.5Hz, 1H, , COCH=CHAr), 6.70(s, 2H, ArH),6.91(d, J=7.5Hz, 1H, ArH), 6.96(s, 1H, ArH), 7.04(d, J=7.5Hz, 1H, ArH), 7.45 (d, J=15.5Hz, 1H, COCH=Ar) |
| 4 | (structure: 3,5-bis(diethylmethyleneoxy)-4-hydroxycinnamide with N-CH$_2$-3,5-di-tert-butyl-4-hydroxyphenyl) | 75–80° C. | 0.97(t, J=7.5Hz, 12H, 4CH$_2$), 1.44(s, 18H, 2C(CH$_3$)$_3$), 1.64–1.78(m, 8H, 4CH$_3$), 4.12–4.18(m, 2H, 2OCH), 4.46(d, J=5.3Hz, 2H, $_2$NH), 5.74(br s, 1H, NH), 5.78(S, 1H, OH), 6.19(d, J=15.5Hz, 1H. CO=CHAr), 6.71(s, 2H, ArH), 7.13(s, 2H, ArH), 7.51 7.51(d, J=15.5Hz, 1H, COCH=Ar) |
| 5 | (structure: 3,5-bis(diethylmethyleneoxy)-4-hydroxycinnamide with N-(CH$_2$)$_3$-3,5-di-tert-butyl-4-hydroxyphenyl) | oil | 0.97(t, J=7.5Hz, 12H, 4CH$_2$), 1.43(s, 18H, 2C(CH$_3$)$_3$), 1.63–1.78(m, 12H, NHCH(CH$_2$)$_2$CH$_2$Ar, 4CH$_2$CH$_3$), 2.56(t, J=6.3Hz, 2H, ArCH$_2$CH$_2$), 3.40(q, J=6.3Hz, 2H, ArCH$_2$CH$_2$NH), 4.12–4.18(m, 2H, 2OCH), 5.74 (Br s, 1H, NH), 5.78(S, 1H, OH), 6.19(d, J=15.5Hz, 1H,COCH=CHAr), 6.71(s, 2H, ArH), 6.93(s, 2H, ArH), 7.48(d, J=15.5Hz, 1H, COCH=CHAr) |
| 6 | (structure: 3,5-bis(pentyloxy)-4-hydroxycinnamide with N-2-hydroxyphenyl) | 137–140° C. | 0.90(t, J=6.7Hz, 6H, 2CH$_2$CH$_3$), 1.26–1.65 (m, 12H, 2(CH$_2$)$_3$×CH$_3$), 1.77–1.86(m, 4H, 2OCH$_2$CH$_2$), 4.05(t, J=6.7Hz, 4H, 2OCH$_2$), 5.80(s, 1H, NH), 6.48(d, J=15.2Hz, 1H, COCH=CHAr), 6.77(s, 2H, ArH), 6.85(t, J=7.1Hz, 1H, ArH), 7.02–7.18(m, 3H, ArH), 7.68(d, J=15.2Hz, 1H, COCH=CHAr), 7.77(s, 1H, OH) |

Example 7

Preparation of 4-{4-[2-(4-fluorophenyl)-2-hydroethyl]piperazine-1-ylmethyl}-2,6-bis-pentyloxyphenol (step 1) Preparation of 1-(4-fluorophenyl)-2-[4-(4-hydroxy-3,5-bis-pentyloxybenzyl)piperazine-1-yl]ethanone To the solution of 4-hydroxymethyl-2,6-bis-pentyloxyphenol (525 mg, 1.62 mmol), 1-(4-fluorophenyl)-2-piperazine-1-yl-ethanone (432 mg, 1.94 mmol) and PPh$_3$ (509 mg, 1.94 mmol) in drying THF (10 ml) was dropped diethyl azodicarboxylate (0.38 ml, 2.43 mmol) at 0° C. and then was stirred 15 minutes at room temperature. The solution was added with H$_2$O, then CH$_2$Cl$_2$ was evaporated in vacuo and was washed with brine. The obtained organic solution was dried over anhydrous magnesium sulfate and filtered. The obtained filtrate was vacuum concentrated to give the residue, which was purified by column chromatography (Hexane:EtOAc=1:10), yielding 129 mg (15%) of 1-(4-fluorophenyl)-2-[4-(4-hydroxy -3,5-bis-pentyloxybenzyl)piperizine-1-yl]ethanone as a yellow oil.

$^1$H NMR (200 MHz, CDCl$_3$) 0.89 (t, J=6.5 Hz, 6H, 2CH3), 1.24–1.43 (m, 12H, 2(CH2)3), 1.76~1.83 (m, 4H, 2CH2), 2.58–2.62 (m, 8H, 2(NCH2CH2)), 3.47 (s, 2H, ArCH2), 3.77 (s, 2H, COCH2), 4.01 (t, J=6.7 Hz, 4H, 2OCH2), 6.54 (s, 2H, ArH), 7.06–7.17 (m, 2H, ArH), 8.01–8.08 (m, 2H, ArH).

(step 2) Preparation of 4-{4-[2-(4-fluorophenyl)-2-hydroethyl]piperazine-1-ylmethyl}-2,6-bis-pentyloxyphenol To the solution of 1-(4-fluorophenyl)-2-[4-(4-hydroxy -3,5-bis-pentyloxybenzyl)piperazine-1-yl]ethanone (120 mg, 0.22 mmol), obtained from the above step 1, in methanol (2 ml) was dropped NaBH,(30 mg, 0.79 mmol) at 0° C. and stirred for 10 minutes. Water was dropped into the solution and then the organic solution was extracted with EtOAc. The obtained organic solution was washed with brine and dried over anhydrous Na$_2$SO$_4$ and filtered. The obtained filtrate was vacuum concentrated to give the residue, which was purified by column chromatography (Hexane:EtOAc=1:10), yielding 70 mg (60 6 of the 4-{4-[2-(4-fluorophenyl)-2-hydroethyl]piperazine-1-ylmethyl}-2,6-bis-pentyloxyphenol as a oil form.

The melting point and $^1$H-NMR data of 4-{4-[2-(4-fluorophenyl)-2-hydroethyl]piperazine-1-ylmethyl}-2,6-bis-pentyloxyphenol are given in Table 2.

Example 8

Preparation of 4-{4-[2-(4-chlorophenyl)-2-hydroethyl]piperazine-1-ylmethyl}-2,6-bis-nonyloxyphenol (step 1) Preparation of 1-(4-chlorophenyl)-2-[4-(4-hydroxy-3,5-bis-nonyloxybenzyl)piperazine-1-yl]ethanone To 4-hydroxy-3,5-bis-nonyloxy benzoic acid (98 mg, 0.23 mmol), 1-(4-chlorophenyl)-2-piperazine-1-yl-ethanone (111 mg, 0.46 mmol), EDCI (89 mg, 0.46 mmol) and HOBT (63 mg, 0.46 mmol) was added MeCN (3 ml) and stirred for 1 hour at room temperature. The solution was added with NaHCO$_3$ to finish the reaction. The solution was extracted with EtOAc, dried over anhydrous Na$_2$SO$_4$ and filtered. The obtained filterate was vacuum concentrated to give the residue, which was purified by column chromatography (Hexane:EtOAc=1:10), yielding 98 mg (66%) of 1-(4-chlorophenyl)-2-[4-(4-hydroxy-3,5-bis-pentyloxybenzoyl)piperizine -1-yl]ethanone.

$^1$H NMR (200 MHz, CDCl$_3$) 0.85~0.91 (m, 6H, 2CH3), 1.22–1.77 (m, 24H, 12CH2), 1.81–1.84 (m, 4H, 2CH2), 2.61 (br s, 4H, 2(NCH2CH2)NCH2), 3.69 (br s, 4H, 2(NCH2CH2)NCH2), 3.82 (s, 2H, CH2CO) 4.03 (t, J=6.6 Hz, 4H, CH2), 6.64 (s, 2H, ArH), 7.46 (d, J=8.7 Hz, 2H, ArH), 7.96 (d, J=8.9 Hz, 2H, ArH).

(step 2) Preparation of 4-{4-[2-(4-chlorophenyl)-2-hydroethyl]piperazine-1-ylmethyl}-2,6-bis-nonyloxyphenyol To the solution of 1-(4-chlorophenyl)-2-[4-(4-hydroxy -3,5-bis-nonyloxybenzoyl)piperazine-1-yl]ethanone (90 mg, 0.14 mmol) obtained from the above step 1, in ether (2 ml) was added LiAlH$_4$ (8 mg, 0.21 mmol) at 0° C. and stirred for 2 hours. Ice water was added to the solution to finish the reaction. The solution was extracted with EtOAc, dried over anhydrous Na$_2$SO$_4$ and filtered. The obtained filtrate was vacuum concentrated to give the residue, which was purified by column chromatography (EtOAc), yielding 16.8 mg (20%) of the 4-{4-[2-(4-chlorophenyl)-2-hydroethyl]piperazine-1-ylmethyl}-2,6-bis-nonyloxyphenol.

The melting point and $^1$H-NMR data of 4-{4-[2-(4-chlorophenyl)-2-hydroethyl]piperazine-1-ylmethyl}-2,6-bis-nonyloxyphenol are given in Table 2.

Example 9

Preparation of 1-{4-[2-(4-chlorophenyl)-2-hydroxyethyl]piperazine-1-yl}-3-(3,5-dibutoxy-4-hydroxyphenyl)propenone (step 1) Preparation of 1-{4-[2-(4-chlorophenyl)-2-oxoethyl]piperazine-1-yl}-3-(3,5-dibutoxy-4-hydroxyphenyl) propenone To 3,5-dibutoxycinnamic acid (220 mg, 0.64 mmol), 4'-chloro-2-(piperazine-1-yl)acetophenone (310 mg, 1.30 mmol), EDCI (250 mg, 1.30 mmol) and HOBT (175 mg, 1.30 mmol) was added MeCN (5 ml) and stirred for 3 hours at room temperature. The solution was added with NaHCO$_3$ to finish the reaction. The solution was extracted with EtOAc, dried over anhydrous Na$_2$SO$_4$ and filtered. The obtained filterate was vacuum concentrated to give the residue, which was purified by column chromatography (Hexane:EtOAc=1:10), yielding 230 mg (68%) of 1-{4-[2-(4-chlorophenyl)-2-oxoethyl]piperazine-1-yl}-3-(3,5-dibutoxy-4-hydroxyphenyl)propenone.

$^1$H NMR (200 MHz, CDCl$_3$) 0.98 (t, J=7.3 Hz, 6H, 2CH3), 1.44~1.55 (m, 4H, 2CH2), 1.74~1.85 (m, 4H, 2CH2), 2.64 (t, J=4.8 Hz, 4H, 2(NCH2CH2)NCH2), 3.62~6.69 (m, 4H, 2(NCH2CH2)NCH2), 3.82 (s, 2H, COCH2), 4.06 (t, J=6.5 Hz, 4H, 2CH2), 6.62 (d, J=15.4 Hz, 1H, CH), 6.73 (s, 2H, ArH), 7.42 (d, J=8.9 Hz, 2H, ArH), 7.53 (d, J=15.4 Hz, 1H, CH), 7.93 (d, J=8.9 Hz, 2H, ArH).

(step 2) Preparation of 1-{4-[2-(4-chlorophenyl)-2-hydroxyehtyl]piperazine-1-yl}-3-(3,5-dibutoxy-4-hydroxyphenyl)propenone To the solution of 1-{4-[2-(4-chlorophenyl)-2-oxoethyl] piperazine-1-yl}-3-(3,5-dibutoxy-4-hydroxyphenyl)propenone (100 mg, 0.19 mmol) obtained from the above step 1, in MeOH (2 ml) was added NaBH$_4$ (25 mg, 0.66 mmol) at 0° C. and stirred for 1 hour. Ice water was added to the solution to finish the reaction. The solution was extracted with EtOAc, dried over anhydrous Na$_2$SO$_4$ and filtered. The obtained filtrate was vacuum concentrated to give the residue, which was purified by column chromatography (EtOAc), yielding 81 mg (80%) of the 1-{4-[2-(4-chlorophenyl)-2-hydroxyehtyl]piperazine-1-yl}-3-(3,5-dibutoxy-4-hydroxyphenyl) propenone as a solid.

The melting point and $^1$H-NMR data of 1-{4-[2-(4-chlorophenyl)-2-hydroxyehtyl]piperazine-1-yl}-3-(3,5-dibutoxy-4-hydroxyphenyl)propenone are given in Table 2.

Example 10

Preparation of 3-(3,5-dibutoxy-4-hydroxyphenyl) -1-{4-[2-(4-fluorophenyl)-2-hydroxyethyl]piperazine-1-yl}propenone (step 1) Preparation of 3-(3,5-dibutoxy-4-hydroxyphenyl)-1-{4-[2-(4-fluorophenyl)-2-oxoethyl]piperazine-1-yl}propenone To 3-(3,5-dibutoxy-4-hydroxyphenyl)acrylic acid (548 mg, 1.77 mmol), 4'-fluoro-2-(piperazine-1-yl)acetophenone (790 mg, 3.55 mmol), EDCI (680 mg, 3.55 mmol) and HOBT (479 mg, 3.55 mmol) was added MeCN (20 ml) and stirred for 30 minutes at room temperature. The solution was diluted with EtOAc and then added with NaHCO, to finish the reaction. The solution was extracted with EtOAc, dried over anhydrous Na$_2$SO$_4$ and filtered. The obtained filterate was vacuum concentrated to give the residue, which was purified by column chromatography (Hexane:EtOAc=1:10), yielding 230 mg (68%) of 3-(3,5-dibutoxy-4-hydroxyphenyl)-1-{4-[2-(4-fluorophenyl)-2-oxoethyl]piperazine-1-yl}propenone as a colorless solid. The melting point of the compound is 49–50° C.

$^1$H NMR (200 MHz, CDCl$_3$) 0.98 (t, J=7.3 Hz, 6H, 2CH3), 1.41~1.55 (m, 4H, 2CH2), 1.75 1.88 (m, 4H, 2CH2), 2.63 (t, J=4.8 Hz, 4H, N(CH2CH2)$_2$NCH2), 3.77 (br s, 4H, N(CH2CH2)2NCH2), 3.83 (s, 2H, COCH2), 4.04 (t, J=6.5 Hz, 4H, 2OCH2), 6.71 (d, J=15.2 Hz, 1H, CH=CHCO), 6.74 (s, 2H, ArH), 7.11~7.18 (m, 2H, ArH), 7.53 (d, J=15.2 Hz, 1H, CH=CHCO), 8.01~8.08 (m, 2H, ArH).

(step 2) Preparation of 3-(3,5-dibutoxy-4-hydroxyphenyl)-1-{4-[2-(4-fluorophenyl)-2-hydroxyethyl]piperazine-1-yl}propenone To the solution of 3-(3,5-dibutoxy-4-hydroxyphenyl)-1-{4-[2-(4-fluorophenyl)-2-oxoethyl]piperazine-1-yl}propenone (530 mg, 1.03 mmol) obtained from the above step 1, in MeOH (10 ml) was added NaBH$_4$ (136 mg, 3.61 mmol) at 0° C. and stirred for 1 hour. Ice water was added to the solution to finish the reaction. The solution was extracted with EtOAc, dried over anhydrous Na$_2$SO$_4$ and filtered. The obtained filtrate was vacuum concentrated to give the residue, which was purified by column chromatography (EtOAc), yielding 460 mg (87%) of the 3-(3,5-dibutoxy-4-hydroxyphenyl)-1-{4-[2-(4-fluorophenyl)-2-hydroxyethyl]piperazine-1-yl}propenone as a solid.

The melting point and ¹H-NMR data of 3-(3,5-dibutoxy-4-hydroxyphenyl)-1-{4-[2-(4-fluorophenyl)-2-hydroxyethyl]piperazine-1-yl}propenone are given in Table 2.

Example 11

Preparation of 1-[4-(2-biphenyl-4-yl-2-hydroxyethyl)piperazine-1-yl]3-(3,5-dibutoxy-4-hydroxyphenyl)propenone (step 1) Preparation of 1-[4-(2-biphenyl-2-oxoethyl)piperazine-1-yl]-3-(4-hydroxy-3,5-dibutoxyphenyl)propenone To 3-(3,5-dibutoxy-4-hydroxyphenyl)acrylic acid (120 mg, 0.39 mmol), 1-biphenyl-4-yl-2-piperazine-1-yl-ethanone (436 mg, 1.55 mmol), EDCI (497 mg, 2.59 mmol) and HOBT (349 mg, 2.59 mmol) was added MeCN (2 ml) and stirred for 1 hour at room temperature. NaHCO₃ was added to the solution to finish the reaction. The solution was extracted with EtOAc, dried over anhydrous Na₂SO₄ and filtered. The obtained filtrate was vacuum concentrated to give the residue, which was purified by column chromatography (Hexane:EtOAc=1:10), yielding 124 mg (56%) of 1-[4-(2-biphenyl-2-oxoethyl)piperazine-1-yl]-3-(4-hydroxy-3,5-dibutoxyphenyl) propenone as a colorless oil ¹H NMR (200 MHz, CDCl₃) 0.98 (t, J=7.3 Hz, 6H, 2CH3), 1.45 1.56 (m, 4H, 2CH2), 1.78~1.85 (m, 4H, 2CH2), 2.64~2.68 (m, 4H, N(CH2CH2)2NCH2), 3.72~3.79 (m, 4H, N(CH2CH2)2NCH2), 3.90 (s, 2H, COCH2), 4.07 (t, J=6.6 Hz, 4H, 2OCH2), 6.72 (d, J=15.2 Hz, 1H, CH=CHCO), 6.74 (s, 2H, ArH), 7.40~7.71 (m, 8H, ArH), 8.05 (d, J=8.5 Hz, 2H, ArH).

(step 2) Preparation of 1-[4-(2-biphenyl-4-yl-2-hydroxyethyl)piperazine-1-yl]3-(3,5-dibutoxy-4-hydroxyphenyl) propenone To the solution of 1-[4-(2-biphenyl-2-oxoethyl)piperazine-1-yl]-3-(4-hydroxy-3,5-dibutoxyphenyl)propenone (100 mg, 0.17 mmol) obtained from the above step 1, in MeOH (2 ml) was added NaBH₄ (22 mg, 0.58 mmol) at 0° C. and stirred for 1 hour. Ice water was added to the solution to finish the reaction. The solution was extracted with EtOAc, dried over anhydrous Na₂SO₄ and filtered. The obtained filtrate was vacuum concentrated to give the residue, which was purified by column chromatography (EtOAc), yielding 75 mg (76%) of the 1-[4-(2-biphenyl-4-yl-2-hydroxyethyl)piperazine-1-yl]3-(3,5-dibutoxy-4-hydroxyphenyl)propenone as a solid.

The melting point and ¹H-NMR data of 1-[4-(2-biphenyl-4-yl-2-hydroxyethyl)piperazine-1-yl]3-(3,5-dibutoxy-4-hydroxyphenyl)propenone are given in Table 2.

Example 12

Preparation of 3-(3,5-bis-hexyloxy-4-hydroxyphenyl)-1-{4-[2-(4-fluorophenyl)-2-hydroxyethyl]piperazine-1-yl}propenone (step 1) Preparation of 1-{4-[2-(4-fluorophenyl)-2-oxoethyl[piperazine-1-yl]-3-(4-hydroxy-3,5-bis-hexyloxyphenyl)propenone To 3-(3,5-dihexyloxy-4-hydroxyphenyl)acrylic acid (350 mg, 0.96 mmol), 1-(4-fluorophenyl)-2-piperazine-1-yl-ethanone (427 mg, 1.92 mmol), EDCT (368 mg, 1.92 mmol) and HOBT (260 mg, 1.92 mmol) was added MeCN (2 ml) and stirred for 1 hour at room temperature. NaHCO₃ was added to the solution to finish the reaction. The solution was extracted with EtOAc, dried over anhydrous Na₂SO₄ and filtered. The obtained filtrate was vacuum concentrated to give the residue, which was purified by column chromatography (Hexane:EtOAc=1:10), yielding 124 mg (56%) of 1-{4-[2-(4-fluorophenyl)-2-oxoethyl[piperazine-1-yl]-3-(4-hydroxy-3,5-bis-hexyloxyphenyl)propenone as a solid. The melting point of the compound is 96–98° C.

¹H NMR (200 MHz, CDCl₃) 0.90 (t, J=6.9 Hz, 6H, 2CH3), 1.33~1.45 (m, 12H, 2(CH2)3), 1.79~1.86 (m, 4H, 2CH2), 2.64 (t, J=4.8 Hz, 4H, N(CH2CH2)2NCH2), 3.79 (br s, 4H, N(CH2CH2)2NCH2), 3.82 (s, 2H, COCH2), 4.06 (t, J=6.6 Hz, 4H, 2OCH2), 5.72 (br s, 1H, OH), 6.70 (d, J=15.2 Hz, 1H, CH=CHCO), 6.73 (s, 2H, ArH), 7.14 (t, J=8.6 Hz, 2H, ArH), 7.53 (d, J=15.2 Hz, 1H, CH=CHCO), 8.01~8.08 (m, 2H, ArH).

(step 2) Preparation of 3-(3,5-bis-hexyloxy-4-hydroxyphenyl)-1-{4-[2-(4-fluorophenyl)-2-hydroxyethyl]piperazine-1-yl}propenone To the solution of 1-{4-[2-(4-fluorophenyl)-2-oxoethyl[piperazine-1-yl]-3-(4-hydroxy-3,5-bis-hexyloxyphenyl) propenone (360 mg, 0.54 mmol) obtained from the above step 1, in MeOH (10 ml) was added NaBH₄ (72 mg, 1.91 mmol) at 0° C. and stirred for 1 hour. Ice water was added to the solution to finish the reaction. The solution was extracted with EtOAc, dried over anhydrous Na₂SO₄ and filtered. The obtained filtrate was vacuum concentrated to give the residue, which was purified by column chromatography (EtOAc), yielding 290 mg (97%) of the 3-(3,5-bis-hexyloxy-4-hydroxyphenyl)-1-{4-[2-(4-fluorophenyl)-2-hydroxyethyl]piperazine-1-yl}propenone as a white solid.

The melting point and ¹H-NMR data of 3-(3,5-bis-hexyloxy -4-hydroxyphenyl)-1-{4-[2-(4-fluorophenyl)-2-hydroxyethyl]piperazine-1-yl}propenone are given in Table 2.

Example 13

Preparation of 3-[3,5-bis-(1-ethylpropoxy)-4-hydroxyphenyl]-1-{4-[2-(4-chlorophenyl)-2-hydroxyethyl]piperazine-1-yl}propenone (step 1) Preparation of 3-[3,5-bis-(1-ethylpropoxy)-4-hydroxyphenyl]-1-{4-[2-(4-chlorophenyl)-2-oxoethyl]piperazine-1-yl}propenone To the solution of 3-(3,5-bis-(1-ethylpropoxy)-4-hydroxyphenyl)acrylic acid (54.7 mg, 0.16 mmol), in THF (1 ml) was added DMF (0.012 ml) and SOCl₂ (0.013 ml). The solution was stirred for 1 hour at same temperature. The solution was added to the solution of 4'-chloro-2-(piperazine-1-yl)acetophenone (39 mg, 0.16 mmol) in drying THF (0.5 ml), stirred for 30 minutes and added with pyridine (0.030 ml, 0.37 mmol). After 30 minutes, the solution was added with toluene (2 ml) and H₂O (2 ml) to finish the reaction. The solution was extracted with EtOAc, dried over anhydrous Na₂SO₄ and filtered. The obtained filtrate was vacuum concentrated to give the residue, which was purified by column chromatography(EtOAc), yielding 17 mg (20%) of 3-[3,5-bis-(1-ethylpropoxy)-4-hydroxyphenyl]-1-{4-[2-(4-chlorophenyl)-2-oxoethyl]piperazine-1-yl}propenone.

¹H NMR (200 MHz, CDCl₃) 0.97 (t, J=7.5 Hz, 12H, 4CH3), 1.65~1.79 (m, 8H, 4CH2), 2.66 (t, J=4.9 Hz, 4H, N(CH2CH2)2NCH2), 3.77 (br s, 4H, N(CH2CH2)2NCH2), 3.84 (s, 2H, CH2CO), 4.14~4.21 (m, 2H, 2CH), 6.67 (d, J=15.2 Hz, 1H, CHCO), 6.72 (s, 2H, ArH).

(step 2) Preparation of 3-[3,5-bis-(1-ethylpropoxy)-4-hydroxyphenyl]-1-{4-[2-(4-chlorophenyl)-2-hydroxyethyl]piperazine-1-yl}propenone To the solution of 3-[3,5-bis-(1-ethylpropoxy)-4-hydroxyphenyl]-1-{4-[2-(4-chlorophenyl)-2-oxoethyl]piperazine-1-yl]propenone (17 mg, 0.03 mmol) obtained from the above step 1, in MeOH (1 ml) was added NaBH₄ (4 mg, 0.10 mmol) at 0° C. and stirred for 1 hour. Ice water was added to the solution to finish the reaction. The solution was extracted with EtOAc, dried over anhydrous Na₂SO₄ and filtered. The obtained filtrate was vacuum concentrated to give the residue, which was purified by TLC (EtOAc), yielding 6.2 mg (37%) of the 3-[3,5-bis-(1-ethylpropoxy)-4-hydroxyphenyl]-1-{4-[2-(4-chlorophenyl)-2-hydroxyethyl]piperazine-1-yl}propenone.

The melting point and ¹H-NMR data of 3-[3,5-bis-(1-ethylpropoxy)-4-hydroxyphenyl]-1-{4-[2-(4-chlorophenyl)-2-hydroxyethyl]piperazine-1-yl}propenone are given in Table 2.

Example 14

Preparation of 3-(4-hydroxy-3,5-bis-nonylphenyl)-1-{4-[2-hydroxy-2-(3-methoxyphenyl)ethyl]piperazine-1-yl}propenone (step 1) Preparation of 1-{4-[2-(3-methoxyphenyl)-2-oxoethyl]piperazine-1-yl}-3-(4-hydroxy-3,5-bis-nonylphenyl)propenone To 3-3,5-dinonyloxy-4-hydroxyphenyl)acrylic acid (150 mg, 0.33 mmol), 1-(3-methoxyphenyl)-2-piperazine-1-yl-ethanone (156 mg, 0.66 mmol), EDCI (128 ml, 0.66 mmol) and HOBT (90 mg, 0.66 mmol) was added drying MeCN (20 ml). The solution was stirred for 30 minutes at room temperature. The solution was diluted with EtOAc and Na₂SO₄ was added to finish the reaction. The solution was extracted with EtOAc, dried over anhydrous Na₂SO₄ and filtered. The obtained filterate was vacuum concentrated to give the residue, which was purified by column chromatography (Hexane:EtOAc=1:10), yielding 88 mg (40%) of 1-[4-[2-(3-methoxyphenyl)-2-oxoethyl]piperazine-1-yl}-3-(4-hydroxy-3,5-bis-nonylphenyl)propenone.

¹H NMR (200 MHz, CDCl₃) 0.88 (t, J=6.4 Hz, 6H, 2CH3), 1.22~1.47 (m, 24H, 2(CH2)6), 1.72~1.79 (m, 4H, 2CH2), 2.66 (t, J=4.9 Hz, 4H, N(CH2CH2)2NCH2), 3.78~3.82 (m, 4H, N(CH2CH2)2NCH2), 3.86 (s, 2H, COCH2), 4.06 (t, J=6.5 Hz, 4H, 2OCH2), 6.71 (d, J=15.2 Hz, 1H, CH=CHCO), 6.73 (s, 2H, ArH), 7.14~7.15 (m, 2H, ArH), 7.37 (t, J=7.8 Hz, 1H, ArH), 7.51~7.61 (m, 2H, ArH).

(step 2) Preparation of 3-(4-hydroxy-3,5-bis-nonylphenyl)-1-{4-[2-hydroxy-2-(3-methoxyphenyl)ethyl]piperazine-1-yl}propenone To the solution of 1-{4-[2-(3-methoxyphenyl)-2-oxoethyl]piperazine-1-yl}-3-(4-hydroxy-3,5-bis-nonylphenyl)propenone (88 mg, 0.13 mmol) obtained from the above step 1, in MeOH (2 ml) was added NaBH₄ (17 mg, 0.46 mmol) at 0° C. and stirred for 10 minutes. Ice water was added to the solution to finish the reaction. The solution was extracted with EtOAc, washed with brine and dried over anhydrous Na₂SO₄ and filtered. The obtained filtrate was vacuum concentrated to give the residue, which was purified by column chromatography (Hexane:EtOAc=1:10), yielding 65 mg (41%) of the 3-(4-hydroxy-3,5-bis-nonylphenyl)-1-{4-[2-hydroxy-2-(3-methoxyphenyl)ethyl]piperazine-1-yl}propenone as a colorless oil.

The melting point and ¹H-NMR data of 3-(4-hydroxy-3,5-bis-nonylphenyl)-1-{4-[2-hydroxy-2-(3-methoxyphenyl)ethyl]piperazine-1-yl}propenone are given in Table 2.

Example 15

Preparation of 1-{4-[2-(4-chlorophenyl)-2-hydroxyethyl]piperazine-1-yl}-3-(3,5-dibutoxy-4-hydroxyphenyl)propane-1-one (step 1) Preparation of 1-{4-[2-(4-chlorophenyl)-2-hydroxyethyl]piperazine-1-yl}-3-(3,5-dibutoxy-4-hydroxyphenyl)-propane-1-one.

To 3,5-dibutoxycinnamic acid (220 mg, 0.64 mmol), 1-(4-chlorophenyl)-2-piperazine-1-yl-ethanone (310 mg, 1.30 mmol), EDCI (250 ml, 1.30 mmol) and HOBT (175 mg, 1.30 mmol) was added drying MeCN (5 ml). The solution was stirred for 30 minutes at room temperature. The solution was diluted with EtOAc and Na₂SO₄ was added to finish the reaction. The solution was extracted with EtOAc, dried over anhydrous Na₂SO₄ and filtered. The obtained filterate was vacuum concentrated to give the residue, which was purified by column chromatography (Hexane:EtOAc=1:10), yielding 88 mg (40%) of 1-{4-[2-]4-chlorophenyl}-2-oxoethyl]piperazine-1-yl}-3-(3,5-dibutoxy-4-hydroxyphenyl) propenone. The melting point of the compound is 45–46° C.

¹H NMR (200 MHz, CDCl₃) 0.98 (t, J=7.3 Hz, 6H, 2CH3), 1.44~1.55 (m, 4H, 2CH2), 1.74~1.85 (m, 4H, 2CH2), 2.64 (t, J=4.8 Hz, 4H, N(CH2CH2)2NCH2), 3.62~6.69 (m, 4H, N(CH2CH2)2NCH2), 3.82 (s, 2H, COCH2), 4.06 (t, J=6.5 Hz, 4H, 2CH2), 6.62 (d, J=15.4 Hz, 1H, CH), 6.73 (s, 2H, ArH), 7.42 (d, J=8.9 Hz, 2H, ArH), 7.53 (d, J=15.4 Hz, 1H, CH), 7.93 (d, J=8.9 Hz, 2H, ArH).

(step 2) Preparation of 1-{4-[2-(4-chlorophenyl)-2-hydroxyethyl]piperazine-1-yl}-3-(3,5-dibutoxy-4-hydroxyphenyl)propane-1-one.

To the solution of 1-{4-[2-{4-chlorophenyl}-2-oxoethyl]piperazine-1-yl}-3-(3,5-dibutoxy-4-hydroxyphenyl)propenone (68 mg, 0.12 mmol) obtained from the above step 1, in MeOH (1.5 ml) was added Pd/C and stirred for 1 hour at room temperature under H₂ gas. The solution was filterated using celite. The obtained filterate was vacuum concentrated to give the residue, which was purified by cloumn chromatography(EtOAc-trace MeOH), yielding 50 mg (78%) of the 1-{4-[2-(4-chlorophenyl)-2-hydroxyethyl]piperazine-1-yl}-3-(3,5-dibutoxy-4-hydroxyphenyl)propane-1-one.

The melting point and ¹H-NMR data of 1-{4-[2-(4-chlorophenyl)-2-hydroxyethyl]piperazine-1-yl}-3-(3,5-dibutoxy-4-hydroxyphenyl)propane-1-one are given in Table 2.

TABLE 2

| example | Compound Name | m.p | $^1$H NMR(CDCl$_3$) |
|---|---|---|---|
| 7 | 4-{4-[2-(4-hydroxyethyl]piperazine-1-ylmethyl}-2,6-bis-pentyloxphenol | oil | 0.90(t, J=6.7Hz, 6H, 2CH$_3$), 1.26–1.49 (m, 12H, 2(CH$_2$)$_3$), 1.77–1.85(m, 4H, 2CH$_2$), 2.42–2.47(m, 8H, 2(NCH$_2$CH$_2$)), 2.67–2.84(m, 2H, CH$_2$), 3.42(s, 2H, ArCH$_2$), 4.03(t, J=6.6Hz, 4H, 2OCH$_2$), 4.61–4.68(m, 1H, CH), 6.53(s, 2H, ArH), 6.98–7.06(m, 2H, ArH), 7.30–737(m, 2H, ArH). |
| 8 | 4-{4-[2-(4-chlorophenyl)-2 hydroxyethyl]piperazine-1-ylmethyl}-2,6-bis-nonyloxphenol | oil | 0.84–0.90(m, 6H, 2CH$_3$), 1.27–1.77(m, 24H, 12CH$_2$), 1.80–1.88(m, 4H, 2CH$_2$), 2.49–2.60 (m, 8H, 4NCH$_2$), 2.84(br s, 2H, CH$_2$), 3.48 (s, 2H, ArCH$_2$), 4.01(t, J = 6.7Hz, 4H, 2OCH$_2$), 4.71–4.78(m, 1H, CH), 5.20(br s, 2H, 2O), 6.53(s, 2H, ArH), 7.30–7.35 (m, 4H, ArH) |
| 9 | 1-{4-[2-(4-chlorophenyl)-2-hydroxyethyl]piperazine-1-yl}-3,5-dibutoxy-4-hydroxyphenol)propenone | 48–51° C. | 0.96(t, J=7.3Hz, 6H, 2CH$_3$), 1.41–1.59 (m, 4H, 2CH$_2$), 1.75–1.85(m, 4H, 2CH$_2$), 2.48–2.53 (m, 4H, (NC$\underline{H}_2$CH$_2$)$_2$NCH$_2$),2.75–2.78(m, 2H, COCH$_2$), 3.75–3.79(m, 4H, (NCH$_2$C$\underline{H}_2$)$_2$NCH$_2$), 4.07(t, J=6.5Hz, 4H, 2CH$_2$), 4.70–4.77 (m, 1H, CH), 6.63(d, J=15.2Hz, 1H, CH=C$\underline{H}$CO), 6.74(s, 2H, ArH), 7.29–7.37(m, 4H, ArH), 7.53(d, J=15.2Hz, 1H, C$\underline{H}$=CHCO) |
| 10 | 3-(3,5-dibutoxy-4-hydroxphenyl)-1-{4-[2-(4-fluorophenyl)-2-hydroxyethyl]piperazine-1-yl}propenone | | 0.99(t, J=7.2Hz, 6H, 2CH$_3$), 1.45–1.59 (m, 4H, 2CH$_2$), 1.75–1.86(m, 4H, 2CH$_2$), 2.49–2.54 (m, 4H, (NC$\underline{H}_2$CH$_2$)$_2$NCH$_2$), 2.76–2.78 (m, 2H, COCH$_2$), 3.73(br s, 4H, (NCH$_2$C$\underline{H}_2$)$_2$NCH$_2$), 4.07 (t,J=6.5Hz, 4H, 2OCH$_2$), 4.67–4.80(m, 1H, CH), 5.71(br s, 1H, OH), 6.71(d, J=15.2Hz, 1H,CH=C$\underline{H}$CO), 6.74(s, 2H, ArH), 7.29–7.37 (m, 4H, ArH), 7.53(d, J=15.2Hz, 1H, C$\underline{H}$=CHCO) |
| 11 | 1-[4-(2-biphenyl-4-yl-2-hydroxyethyl)piperazine-1-yl]3-(3,5-dibutoxy-4-hydroxyphenyl)propenone | 66–67° C. | 0.98(t, J=7.3Hz, 6H, 2CH$_3$), 1.41–1.60 (m, 4H, 2CH$_2$), 1.75–1.89(m, 4H, 2CH$_2$), 2.58–2.62 (m, 4H, (NC$\underline{H}_2$CH$_2$)$_2$NCH$_2$), 2.78–2.81 (m, 2H, CH$_2$), 3.75(br s, 4H, (NCH$_2$C$\underline{H}_2$)$_2$NCH$_2$),4.07 (t, J=6.5Hz, 4H, 2OCH$_2$), 4.79–4.91(m, 1H, CH), 5.70(br s, 1H, OH), 6.72(d, J=15.0Hz, 1H,CH=C$\underline{H}$CO), 6.74(s, 2H, ArH), 7.30–7.66 (m, 10H, ArH) |

TABLE 2-continued

| example | Compound Name | m.p | $^1$H NMR(CDCl$_3$) |
|---|---|---|---|
| 12 | 3-(3,5-bis-hexyloxy-4-hydroxphenyl)-1-{4-[2-(4-fluorophenyl)-2-hydroxyethyl]piperazine-1-yl}propenone | 120–121° C. | 0.90(t, J=6.8Hz, 6H, 2CH$_3$), 1.34–1.47 (m, 12H, 2(CH$_2$)$_3$), 1.76–1.87(m, 4H, 2CH$_2$), 2.51–2.54(m, 4H, N(CH$_2$CH$_2$)$_2$NCH$_2$), 2.76–2.82 (m, 2H, CH$_2$),3.74(br s, 4H, N(CH$_2$ CH$_2$)$_2$NCH$_2$), 4.06(t, J=6.7Hz, 4H, 2OCH$_2$), 4.69–4.80 (m, 1H, CH), 5.70(br s, 1H, OH), 6.71 (d, J=15.1Hz,H, CH=CHCO), 6.73(s, 2H, ArH), 7.03 (t, J=8.6Hz, 2H, ArH), 7.31–7.38 (m, 2H, ArH), 7.54(d, J=15.1Hz, 1H, CH=CHCO) |
| 13 | 3-[3,5-bis(1-ethylpropoxyl)-4-hydroxphenyl]-1-{4-[2-(4-chlorophenyl)-2-hydroxethyl]piperazin-1-yl}propenone | oil | 0.98(t, J=7.4Hz, 12H, 4CH$_3$), 1.65–1.79 (m, 8H, 4CH$_2$), 2.46–2.55(m, 8H, 4NCH$_2$CH$_2$), 2.76–2.79(m, 2H, CH$_2$), 4.15–4.21(m, 2H, 2CH), 4.71–4.90(m, 1H, CH), 6.67(d, J=15.2Hz, 1H, CH=CHCO), 6.72(s, 2H, ArH), 7.32–7.36(m, 5H, Ar), 7.60(d, J=15.2Hz, 1H, CH=CHCO) |
| 14 | 3-(4-hydroxy-3,5-bis-nonylphenyl)-1-{4-[2-hydroxy-2-(3-methoxyphenyl)ethyl]piperazine-1-yl}propenone | oil | 0.88(t, J=6.4Hz, 6H, 2CH$_3$), 1.22–1.45 (m, 24H, 2(CH$_2$)$_6$), 1.79–1.86(m, 4H, 2CH$_2$), 2.53–2.57(m, 4H, (NCH$_2$CH$_2$)$_2$NCH$_2$), 2.69–2.84 (m, 2H, CH$_2$), 3.73(br s, 4H,(NCH$_2$ CH$_2$)$_2$NCH$_2$), 3.81(s, 3H, OCH$_3$), 4.06(t, J=6.6Hz, 4H, 2OCH$_2$), 4.72–4.81(m, 1H, CH), 6.71(d, J=15.2Hz, 1H,CH=CHCO), 6.74(s, 2H, ArH), 6.85–6.95(m, 2H, ArH), 7.26(t, J=7.7Hz, 1H, ArH), 7.54(d, J=15.2Hz, 1H, CH=CHCO) |
| 15 | 1-{4-[2-(4-chlorophenol)-2-hydroxyethyl]piperazine-1-yl}-3-(3,5-dibutoxy-4-hydroxphenyl)propane-1-one | oil | 0.96(t, J=7.3Hz, 6H, 2CH$_3$), 1.38–1.57 (m, 4H, 2CH$_2$), 1.71–1.90(m, 4H, 2CH$_2$), 2.50–2.65 (m, 4H, 2NCH$_2$), 2.82–2.90(m, 2H, COCH$_2$), 3.42–3.45(m, 2H, N—CH$_2$), 3.66–3.70 (m, 2H, N—CH$_2$), 4.00(t, J=7.1Hz, 4H, 2CH$_2$), 4.73–4.79(m, 1H, CH),5.26(br s, 1H, OH), 6.41(s, 2H, ArH), 7.25–7.41(m, 8H, ArH) |

Example 16

Preparation of N-(4-(4-[3-(3,5-di-t-butyl-4-hydroxyphenyl)-acryloyl]-piperizine-lyl}-phenyl)-thiophene-2-carboxamidine (step 1) Preparation of 3-(3,5-di-t-butyl-4-hydroxy-phenyl)-1-[4-(4-nitro-phenyl)-piperizine-1-yl]-propenone In a 100 ml round flask, 3-(3,5-di-t-butyl-4-hydroxyphenyl)-acryloic acid (2.00 g, 7.24 mmol), 1-(4-nitrophenyl) piperizine (1.50 g, 7.24 mmol), EDCI (6.94 g, 36.2 mmol) and HOBT (4.89 g, 36.2 mmol) were dissolved in purified CH$_3$CN and then the solution was stirred for 3 hours at room temperature. CH$_3$CN was removed and CH$_2$Cl$_2$ was added. The solution was washed with NaHCO$_3$ and further washed with brine and water. The obtained organic solution was dried over Na$_2$SO$_4$, and filterated. The obtained filtrate was vacuum concentrated to give the residue, which was purified by column chromatography (Hexane:EtOAc=2:1), yielding 2.854 g (85%) of 3-(3,5-di-t-butyl-4-hydroxy-phenyl)-1-[4-(4-nitro-phenyl)-piperizine-1-yl]-propenone. The melting point of the compound is 105–106° C.

$^1$H NMR (200 Hz, CDCl3) 1.47 (s, 18H, 6CH3), 3.50–3.55 (m, 4H, 2NCH2), 3.88–3.91 (m, 4H, 2NCH2), 5.49 (s, 1H, OH), 6.68 (d, J=15.3 Hz, 1H, COCH=CH), 6.84 (d, J=9.4 Hz, 2H, 2ArH), 7.37 (s, 2H, 2ArH), 7.70 (d, J=15.1 Hz, 1H, ArCH=CH), 8.16 (d, J=9.4 Hz, 2H, 2ArH)

(step 2) Preparation of 1-[4-(4-amino-phenyl)-piperazine-1-yl]-3-(3,5-di-t-butyl-4-hydroxy-phenyl)-prpenone In a 50 ml round flask, 3-(3,5-di-t-butyl-4-hydroxy-phenyl)-1-[4-(4-nitro-phenyl)-piperazine-1-yl]-propenone (500 mg, 1.07 mmol) and Fe (powder) (480 mg, 8.59 mmol) were dissolved in the purified EtOH and HCL (1.30 ml, 15.0 mmol) was slowly to the mixture and then stirred for 4 hours at room temperature. The solution was added with CH$_2$Cl$_2$, washed with NaHCO$_3$ and further washed with brine and water. The water in the organic solution was dried over Na$_2$SO$_4$ and filtered. The obtained filtrate was vacuum concentrated to give the residue, which was purified by column chromatography (Hexane:EtOAc=1:1), yielding 243 mg (52%) of 1-[4-(4-amino-phenyl)-piperazine-1-yl]-3-(3,5-di-t-butyl-4-hydroxy-phenyl)-prpenone. The melting point of the compound is 81–82° C.

$^1$H NMR (200 Hz, CDCl3) 1.47 (s, 18H, 6CH3), 3.07 (t, J=5.1 Hz, 4H, 2NCH2), 3.84(bs, 4H, 2NCH2), 6.67 (d, J=8.5 Hz, 2H, 2ArH), 6.73 (d, J=14.4 Hz, 1H, COCH=CH), 6.84 (d, J=8.5 Hz, 2H, 2ArH), 7.37 (s, 2H, 2ArH), 7.67 (d, J=14.4 Hz, 1H, ArCH=CH).

(step 3) Preparation of N-(4-{4-[3-(3,5-di-t-butyl-4-hydroxy-phenyl)-acryloyl]-piperazine-1-yl}-phenyl_thiophene-2-carboxamidine In a 50 ml round flask, 1-[4-(4-amino-phenyl)-piperazine-1-yl]-3-(3,5-di-t-butyl-4-hydroxy-phenyl)-propenone (200 mg, 0.46 mmol) was dissolved in pyridine, and 1,1,1,3,3,3,-hexamethyldisilazane (2.30 ml, 10.7 mmol) and trimethylchlorosilane (2.00 ml, 16.1 mmol) were dropped and then refluxed for 3 hours. After cooling to room temperature, water was added to the solution to finish the reaction. CH$_2$Cl$_2$ was extracted and washed with brine and water. The water in the organic solution was dried over Na$_2$SO$_4$, filterated and vacuum concentrated. The concentrated compound and methylsulfanyl-2-thienyl methanimine HI salt (11 mg, 0.04 mmol) were dissolved in chloroform (0.50 ml), acetic acid was dropped and then stirred for 5 hours at room temperature. After removing Chloroform, EtOAc was dissolved in the solution, washed with NaHCO$_3$ and further washed with brine and water. Tetrabutylammonium fluoride (2 ml) was dropped into the organic solution and stirred for 20 minutes at room temperature. The obtained solution was washed with brine and water and the water was dried over Na$_2$SO$_4$ and filtered. The obtained filtrate was vacuum concentrated to give the residue, which was purified by column chromatography (Hexane:EtOAc=1:1), yielding 9 mg (87%) of the N-(4-{4-[3-(3,5-di-t-butyl-4-hydroxy-phenyl)-acryloyl]-piperazine-1-yl}-phenyl-thiophene-2-carboxamidine.

The melting point and $^1$H-NMR data of N-(4-[4-{3-(3,5-di-t-butyl-4-hydroxy-phenyl)-acryloyl]-piperazine-1-yl}-phenyl-thiophene-2-carboxamidine are given in Table 3.

Example 17

Preparation of N-[4-(4-{3-[3,5-bis-(1-ethyl-propoxy)-4-hydroxy-phenyl]-acryloyl}-piperazine-1-yl-phenyl)-thiophene-2-carboxamidine (step 1) Preparation of 3-[3,5-bis-(1-ethyl-propoxy)-4-hydroxy-phenyl]-1-[4-(4-nitro-phenyl)-piperazine-1-yl]-propenone The title compound was obtained in the same manner as in the above step 1 of example 16. Yield 457 mg (73%).

$^1$H-NMR (200 Hz, CDCl3) 0.98 (t, J=7.3 Hz, 12H, 4CH3), 1.70(qui, J=6.9 Hz, 8H, 4CH2), 3.52(bs, 4H, 2CH2), 3.89(bs, 4H, 2CH2), 4.19 (t, J=5.7 Hz, 2H, 2CH), 5.82 (s, 1H, OH), 6.65 (d, J=15.5 Hz, 1H, CHCH), 6.74 (s, 2H, 2ArH), 6.83 (d, J=9.4 Hz, 2H, 2ArH), 7.62 (d, J=15.5 Hz, 1H, CHCH), 8.14 (d, J=9.4 Hz, 2H, 2ArH).

(step 2) Preparation of 1-[4-(4-amino-phenyl)-piperazine-1-yl]-3-[3,5-bis-(1-ethyl-propoxy)-4-hydroxy-phenyl]-propenone The title compound was obtained in the same manner as in the above step 2 of example 16. Yield 383 mg (92%)

$^1$H-NMR (200 Hz, CDCl3) 0.97 (t, J=7.3 Hz, 12H, 4CH3), 1.70(qui, J=6.9 Hz, 8H, 4CH2), 3.05 (t, J=5.1 Hz, 4H, 2CH2), 3.82(bs, 4H, 2CH2), 4.18(qui, J=5.7 Hz, 2H, 2CH), 6.65 (d, J=8.9 Hz, 2H, 2ArH), 6.68 (d, J=15.3 Hz, 1H, CHCH), 6.72 (s, 2H, 2ArH), 6.81 (d, J=8.7 Hz, 2H, 2ArH), 7.57 (d, J=15.3 Hz, 1H, CHCH).

(step 3) Preparation of N-[4-(4-{3-[3,5-bis-(1-ethyl-propoxy)-4-hydroxy-phenyl]-acryloyl}-piperazine-1-yl-phenyl)-thiophene-2-carboxamidine The title compound was obtained in the same manner as in the above step 3 of example 16. Yield 213 mg (50%).

The melting point and $^1$H-NMR data of N-[4-(4-{3-[3,5-bis-(1-ethyl-propoxy)-4-hydroxy-phenyl]-acryloyl}-piperazine-1-yl-phenyl)-thiophene-2-carboxamidine are given in Table 3.

Example 18

Preparation of N-(4-{4-[3-(4-hydroxy-3,5-dipropoxy-phenyl)-acryloyl]-piperazine-1-yl}-phenyl)-thiophene-2-carboxamidine (step 1) Preparation of 3-(4-hydroxy-3,5-dipropoxy-phenyl)-1-[4-(4-nitro-phenyl)-piperazine-1-yl]-propenone In a 100 ml round flask, 3-(4-hydroxy-3,5-dipropoxy-phenyl)-acrylic acid (330 mg, 1.14 mmol), 1-(4-nitrophenyl) piperazine (237 mg, 1.14 mmol), EDCI (438 mg, 2.28 mmol) and HOBT (309 mg, 2.28 mmol) were dissolved in CH$_3$CN and reacted for one night at room temperature. CH$_3$CN was removed and CH$_2$Cl$_2$ was added. The solution was washed with NaHCO$_3$ and further washed with brine and water. The obtained organic solution was dried over Na$_2$SO$_4$, and filtered. The obtained filtrate was vacuum concentrated to give the residue, which was purified by column chromatography (Hexane:EtOAc=2:1), 3-(4-hydroxy-3,5-dipropoxy-phenyl)-1-[4-(4-nitro-phenyl)-piperazine-1-yl]-propenone.

(step 2) Preparation of 1-[4-(4-amino-phenyl)-piperazine-1-yl]-3-(4-hydroxy-3,5-dipropoxy-phenyl)-propenone The title compound was obtained in the same manner as in the above step 2 of example 16. Yield 403 mg (80%) Melting point 72–73° C.

$^1$H-NMR (200 Hz, CDCl3) 1.05 (t, J=7.3 Hz, 6H, 2CH3), 1.86 (sex, J=7.1 Hz, 4H, 2CH2), 3.05 (t, J=4.9 Hz, 4H, 2NCH2), 3.48 (bs, 2H, NH2), 3.83 (bs, 4H, 2NCH2), 4.04 (t, J=6.7 Hz, 4H, 2OCH2), 5.70 (bs, 1H, ArOH), 6.66 (d, J=8.9 Hz, 2H, 2ArH), 6.71 (d, J=15.1 Hz, 1H, COCH=CH), 6.75 (s, 2H, 2ArH), 6.81 (d, J=8.9 Hz, 2H, 2ArH), 7.58 (d, J=15.1 Hz, 1H, ArCH=CH).

(step 3) Preparation of N-(4-{4-[3-(4-hydroxy-3,5-dipropoxy-phenyl)-acryloyl]-piperazine-1-yl}-phenyl)-thiophene-2-carboxamidine The title compound was obtained in the same manner as in the above step 3 of example 16. Yield 120 mg (38%).

The melting point and $^1$H-NMR data of N-(4-{4-[3-(4-hydroxy-3,5-dipropoxy-phenyl)-acryloyl]-piperazine-1-yl}-phenyl)-thiophene-2-carboxamidine are given in Table 3.

Example 19

Preparation of N-(4-{4-[3-(3,5-dibutoxy-4-hydroxy-phenyl)-acryloyl]-piperazine-1-yl}-phenyl)-thiophene-2-carboxamidine (step 1) Preparation of 3-(3,5-diboutoxy-4-hydroxy-phenyl)-1-[4-(4-nitro-phenyl-1-piperazine-1-yl)-propenone The title compound was obtained in the same manner as in the above step 1 of example 16. Yield 194 mg (67%). Melting point 191–193° C.

$^1$H-NMR (200 Hz, CDCl3) 0.99 (t, J=7.3 Hz, 6H, 2CH3), 1.51(sex, J=7.4 Hz, 4H, 2CH2) 1.83(qui, J=7.0 Hz, 4H, 2CH2), 3.52 (t, J=5.2 Hz 4H, 2NCH2), 3.88–3.90 (m, 4H, 2NCH2), 5.71(bs, 1H, OH), 6.69 (d, J=15.3 Hz, 1H, COCH=CH), 6.76 (s, 2H, 2ArH), 6.83 (d, J=9.5 Hz, 2H, 2ArH), 7.63 (d, J=15.3 Hz, 1H, ArCH=CH), 8.15 (d, J=9.5 Hz, 2H, 2ArH).

(step 2) Preparation of 1-[4-(4-amino-phenyl)-piperazine-1-yl]-3-(3,5-dibutoxy-4-hydroxy-phenyl)-propenone The title was obtained in the same manner as in the above step 2 of example 16. Yield 140 mg (86%) Melting point 65–68° C.

$^1$H-NMR (200 Hz, CDCl3) 0.99 (t, J=7.4 Hz, 6H, 2CH3), 1.51(sex, J=7.3 Hz, 4H, 2CH2), 1.83(qui, J=7.0 Hz, 4H, 2CH2), 3.06 (t, J=5.1 Hz, 4H, 2NCH2), 3.84(bs, 4H, 2NCH2), 6.67 (d, J=8.9 Hz, 2H, 2ArH), 6.72 (d, J=15.5 Hz, 1H, COCH=CH), 6.76 (s, 2H, 2ArH), 6.82 (d, J=8.9 Hz, 2H, 2ArH), 7.59 (d, J=15.5 Hz, 1H, ArCH=CH).

(step 3) Preparation of N-(4-t4-[3-(3,5-dibutoxy-4-hydroxy-phenyl)-acryloyl]-piperazine-1-yl}-phenyl)-thiophene-2-carboxamidine The title compound was obtained in the same manner as in the above step 3 of example 16. Yield 118 mg (74%).

The melting point and $^1$H-NMR data of N-(4-{4-[3-(3,5-dibutoxy-4-hydroxy-phenyl)-acryloyli]-piperazine-1-yl}-phenyl)-thiophene-2-carboxamidine are given in Table 3.

Example 20

Preparation of N-(4-{4-[3-(4-hydroxy-3,5-bis-nonyl-phenyl)-acryloyl]-piperazine-1-yl}-phenyl)-thiophene-2-carboxamidine (step 1) Preparation of 3-(4-hydroxy-3,5-bis-nonyloxy-phenyl)-1-[4-(4-nitro-phenyl)-[piperazine-1-yl]-propenone The title compound was obtained in the same manner as in the above step 1 of example 16. Yield 525 mg (72%) Melting point 103–105° C.

$^1$H-NMR (200 Hz, CDCl3) 0.88 (t, J=6.5 Hz, 6H, 2CH3), 1.27–1.45 (m, 24H, 10CH3), 1.83(qui, J=7.0 Hz, 4H, 2CH2), 3.51 (t, J=5.2 Hz, 4H, 2NCH2), 3.90 (t, J=5.2 Hz, 4H, 2NCH2), 4.06 (t, J=6.6 Hz, 4H, 2OCH2), 5.75 (s, 1H, OH), 6.69 (d, J=15.5 Hz, 1H, COCH=CH), 6.76 (s, 2H, 2ArH), 6.82 (d, J=9.4 Hz, 2H, 2ArH), 7.62 (d, J=15.5 Hz, 1H, ArCH=CH), 8.14 (d, J=9.4 Hz, 2H, 2ArH).

(step 2) Preparation of 1-[4-(4-amino-phenyl)-piperazine-1-yl]-3-(4-hydroxy-3,5-bis-nonyloxy-phenyl)-propenone The title compound was obtained in the same manner as in the above step 2 of example 16. Yield 390 mg (82%) Melting point 110–111° C.

$^1$H-NMR (200 Hz, CDCl3) 0.88 (t, J=6.5 Hz, 6H, 2CH3), 1.27–1.45 (m, 24H, 10CH3), 1.83(qui, J=7.0 Hz, 4H, 2CH2), 3.05 (t, J=5.2 Hz, 4H, 2NCH2), 3.46(bs, 2H, NH2), 3.83(bs, 4H, 2NCH2), 4.06 (t, J=6.6 Hz, 4H, 2OCH2), 5.70(bs, 1H, OH), 6.64 (d, J=8.9 Hz, 2H, 2ArH), 6.71 (d, J=15.1 Hz, 1H, COCH=CH), 6.75 (s, 2H, 2ArH), 6.82 (d, J=8.9 Hz, 2H, 2ArH), 7.59 (d, J=15.1 Hz, 1H, ArCH=CH).

(step 3) Preparation of N-(4-{4-[3-(4-hydroxy-3,5-bis-nonyl-phenyl)-acryloyl]-piperazine-1-yl}-phenyl)-thiophene-2-carboxamidine The title compound was obtained in the same manner as in the above step 3 of example 16. Yield 360 mg (79%).

The melting point and $^1$H-NMR data of N-(4-{4-[3-(4-hydroxy-3,5-bis-nonyl-phenyl)-acryloyl]-piperazine-1-yl}-phenyl)-thiophene-2-carboxamidine are given in Table 3.

Example 21

Preparation of N-(4-{4-[3-(3,5-di-t-butyl-4-hydroxy-phenyl)-acryloyl]-piperazine-1-yl}-phenyl)-1H-pyrrole-2-carboxamidine In 50 ml round flask, 1-[4-(4-amino-phenyl)-piperazine-1-yl]-3-(3,5-t-butyl-4-hydroxy-phenyl)-propenone (600 mg, 1.38 mmol) was dissloved in pyridine and then 1,1,1,3,3,3-hexamethyldisilazane (2.90 ml, 13.8 mmol) and trimethylchlorosilane (2.60 ml, 20.7 mmol) were dropped into the solution. The solution was refluxed for 3 hours. After cooling it to room temperature, water was added to the solution to finish the reaction. The solution was extracted with $CH_2Cl_2$ and washed with brine and water. The water was dried over $Na_2SO_4$ and filtered. After the obtained filtrate was vacuum concentrated, 1H-2-azolyl-methylsulfanyl methanimine HI salt (406 mg, 1.52 mmol) was added and dissolved in purified 2-propanol (10 ml). The solution was stirred for one night at room temperature. After removing 2-propanol, EtOAc was added, and the mixture was washed with $NaHCO_3$ and further washed with brine and water. Tetrabutylammonium fluoride (2 ml) was dropped into the organic solution and stirred for 20 minutes at room temperature. The solution was washed with brine and water, and the water in the solution was dried over $Na_2SO_4$ and filtered. The obtained filtrate was vacuum concentrated to give the residue, which was purified by column chromatography (MeOH:EtOAc=1:10), yielding 527 mg (72%) of N-(4-{4-[3-(3,5-di-t-butyl-4-hydroxy-phenyl)-acryloyl]-piperazine-1-yl}-phenyl)-1H-pyrrole-2-carboxamidine.

The melting point and ¹H-NMR data of N-(4-{4-[3-(3,5-di-t-butyl-4-hydroxy-phenyl)-acryloyl]-piperazine-1-yl}-phenyl) -1H-pyrrole-2-carboxamidine are given in Table 3.

Example 22

Preparation of N-(4-{4-[3-(3,5-dibutoxy-4-hydroxy-phenyl)-acryloyl]-piperazine-1-yl}-phenyl)-1H-pyrrole-2-carboxamidine The title compound was obtained in the same manner as in the above step 3 of example 21. Yield 102 mg (22%).

The melting point and ¹H-NMR data of N-(4-{4-[3-(3,5-dibutoxy-4-hydroxy-phenyl)-acryloyl]-piperazine-1-yl}-phenyl)-1H-pyrrole-2-carboxamidine are given in Table 3.

Example 23

Preparation of N-(4-{4-[3-(4-hydroxy-3,5-bis-penyloxy-phenyl)-acryloyl]-piperazine-1-yl}-phenyl)-1H-pyrrole-2-carboxamidine The title compound was obtained in the same manner as in the above step 3 of example 21. Yield 492 mg (73%).

The melting point and ¹H-NMR data of N-(4-{4-[3-(4-hydroxy-3,5-bis-penyloxy-phenyl)-acryloyl]-piperazine-1-yl}-phenyl)-1H-pyrrole-2-carboxamidine are given in Table 3.

Example 24

Preparation of N-(4-{4-[3-(3,5-bis-heptyloxy-4-hydroxy-phenyl)-acryloyl]-piperazine-1-yl}-phenyl)-1H-pyrrole-2-carboxamidine The title compound was obtained in the same manner as in the above step 3 of example 21. Yield 504 mg (66%).

The melting point and ¹H-NMR data of N-(4-{4-[3-(3,5-bis-heptyloxy-4-hydroxy-phenyl)-acryloyl]-piperazine-1-yl}-phenyl)-1H-pyrrole-2-carboxamidine are given in Table 3.

TABLE 3

| example | structure | m.p. | ¹H NMR(CDCl₃) |
|---|---|---|---|
| 16 | 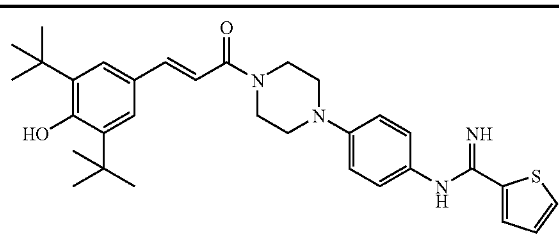 | oil | 1.46(s, 18H, 6CH₃), 3.16(t, J=5.1Hz, 4H, 2CH₂), 3.87(bs, 4H, 2CH₂), 4.83(bs, 2H, 2NH), 6.72(d, J=15.5Hz, 1H, COC$\underline{H}$=CH), 6.95(s, 4H, 4ArH), 7.07(t, J=3.7Hz, 1H, thiophene CH), 7.37(s, 2H, 2ArH), 7.41(m, 2H, thiophene 2CH), 7.67(d, J=15.3Hz, 1H, ArC$\underline{H}$=CH) |
| 17 | 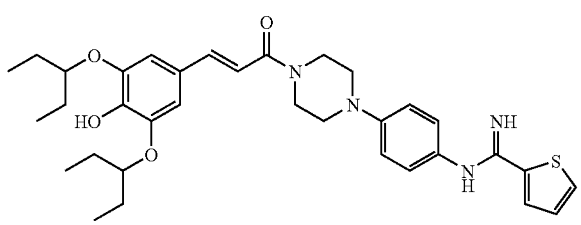 | 170–171° C. | 0.94(t, J=6.5Hz, 12H, 4CH₃) 1.72(qui, J=7.0Hz, 8H, 4CH₂), 3.19(bs. 4H, 2CH₂), 3.85(bs, 4H, 2CH₂), 4.19(qui, J=5.9Hz, 2H, 2CH), 4.89(bs, 2H, 2NH), 6.70(d, J=15.5Hz, 1H, COC$\underline{H}$=CH), 6.74(s, 2H, 2ArH), 6.94(s, 4H, 4ArH), 7.05(t, J=3.9Hz, 1H, thiophene CH), 7.40(d, J=4.1Hz, 2H, thiophene 2CH), 7.58(d, J=15.1Hz, 1H, ArC$\underline{H}$=CH) |
| 18 | 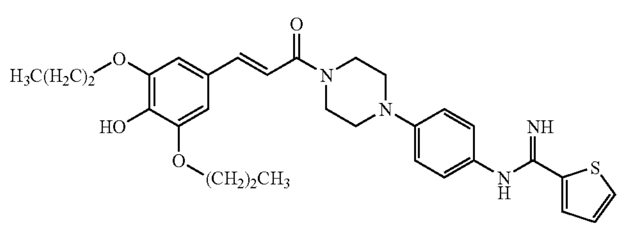 | 188–189° C. | 0.93(t, J=6.7Hz, 6H, 2CH₃), 1.34–1.50 (m, 8H, 4CH₂), 1.84(qui, J=6.8Hz, 4H, 2CH₂), 3.18(t, J=5.0Hz, 4H, 2NCH₂), 3.86 (bs, 4H, 2NCH₂), 4.07(t, J=6.6Hz, 4H, 2OCH₂), 6.72(d, J=15.1Hz, 1H, COC$\underline{H}$=H), 6.75(s, 2H, 2ArH), 6.95(s, 4H, 4ArH), 7.05–7.10(m, 1H, thiophene CH), 7.40–7.44 (m, 2H, thiophene 2CH), 7.59 (d, J=15.1Hz, 1H, ArC$\underline{H}$=CH) |
| 19 | 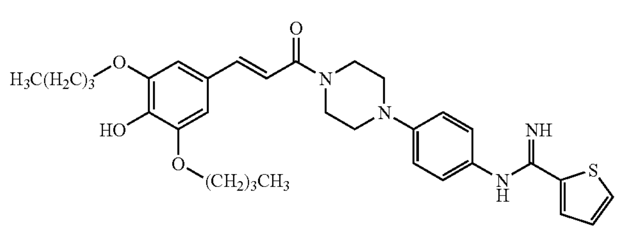 | 99–102° C. | 0.99(t, J=7.4Hz, 6H, 2CH₃), 1.50(sex, J=7.3Hz, 4H, 2CH₂), 1.83(qui, J=7.0Hz, 4H, 2CH₂), 3.18(t, J=4.9Hz, 4H, 2NCH₂), 3.86(bs, 4H, 2NCH₂), 4.08(t, J=6.5Hz, 4H, 2OCH₂), 4.81(bs, 2H, 2NH), 6.72(d, J=15.5Hz, 1H, COC$\underline{H}$=CH), 6.78(s, 2H, 2ArH), 6.95(s, 4H, 4ArH), 7.07(t, J=4.9Hz, 1H, thiophene CH), 7.38–7.43(m, 2H, thiophene2CH), 7.61(d, J=15.5Hz, 1H, ArC$\underline{H}$=CH) |

TABLE 3-continued

| example | structure | m.p. | ¹H NMR(CDCl₃) |
|---|---|---|---|
| 20 | | 154–155° C. | 0.88(t, J=6.5Hz, 6H, 2CH₃), 1.27–1.45(m, 24H, 10CH₃), 1.83(qui, J=17.0Hz, 4H, 2CH₂), 3.18(bs, 4H, 2NCH₂), 3.87(bs, 4H, 2NCH₂), 4.07(t, J=6.6Hz, 4H, 2OCH₂), 4.80(bs, 2H, 2NH), 6.71(d, J=15.1Hz, 1H, COC<u>H</u>=CH), 6.76(s, 2H, 2ArH), 6.96(s, 4H, 4ArH), 7.07(t, J=4.5Hz, 1H, thiophene CH), 7.39–7.43(m, 1H, thiophene 2CH), 7.60(d, J=15.1Hz, 1H, ArC<u>H</u>=CH) |
| 21 | | 149–167° C. | 1.46(s, 18H, 6CH₃), 3.18(t, J=15.1Hz, 4H, 2NCH₂), 3.86(bs, 4H, 2NCH₂), 4.72 (bs, 3H, 3NH), 6.23–6.26(m, 1H, pyrrole CH), 6.51–6.52(m, 1H, pyrrole CH), 6.72 (d, J=15.1Hz, 1H, COC<u>H</u>=CH), 6.87(s, 1H, pyrrole CH), 6.94(s, 4H, 4ArH), 7.37(s, 2H, 2ArH), 7.67(d, J=15.1Hz, 1H, <u>Ar</u>CH=CH) |
| 22 | | 120–128° C. | 0.99(t, J=7.2Hz, 6H, 2CH₃), 1.51(sex, J=7.5Hz, 4H, 2CH₂), 1.83(qui, J=7.0Hz, 4H, 2CH₂), 3.18(bs, 4H, 2NCH₂), 3.87(bs, 4H, 2NCH₂), 4.08(t, J=6.5Hz, 4H, 2OCH₂), 4.79(bs, 3H, 3NH), 6.22–6.24(m, 1H, pyrrole CH), 6.52–6.54(m, 1H, pyrrole CH), 6.72(d, J=15.3Hz, 1H, COC<u>H</u>=CH), 6.76(s, 2H, 2ArH), 6.86(s, 1H, pyrrole CH), 6.95(s, 4H, 4ArH), 7.60(d, J=15.3Hz, 1H, ArC<u>H</u>=CH) |
| 23 | | 109–116° C. | 0.93(t, J=6.7Hz, 6H, 2CH₃), 1.34–1.50 m, 8H, 4CH₂), 1.84(qui, J=6.8Hz, 4H, 2CH₂), 3.17(s, 4H, 2NCH₂), 3.86(bs, 4H, 2NCH₂), 4.06(t, J=6.6Hz, 4H, 2OCH₂), 4.96(bs, 3H, 3NH), 6.21–6.24(m, 1H, pyrrole CH), 6.54–6.56(m, 1H, pyrrole CH), 6.72(d, J=15.4Hz, 1H, COC<u>H</u>=CH), 6.75(s, 2H, 2ArH), 6.85(s, 1H, pyrrole CH), 6.94(s, 4H, 4ArH), 7.60(d, J=15.4Hz, 1H, ArC<u>H</u>=CH) |
| 24 | | 100–145° C. | 0.89(t, J=6.7Hz, 6H, 2CH₃), 1.30–1.42 (m, 16H, 8CH₂), 1.83(qui, J=6.9Hz, 4H, 2CH₂), 3.17(bs, 4H, 2NCH₂), 3.86(bs, 4H, 2NCH₂), 4.06(t, J=6.6Hz, 4H, 2OCH₂), 5.06(bs, 3H, 3NH), 6.21–6.24(m, 1H, pyrrole CH), 6.54–6.56(m, 1H, pyrrole CH), 6.72(d, J=15.5Hz, 1H, COC<u>H</u>=CH), 6.75(s, 2H, 2ArH), 6.84(s, 1H, pyrrole J=15.5Hz, 1H, ArC<u>H</u>=CH) |

Preparation Example 1

Preparation of Tablet

A tablet containing the cinnamic acid of the present invention as an effective ingredient was prepared according to the following processes.

The compound of the above example 1 was sieved, mixed with lactose starch and pregelatinized corn starch. To the mixture, purified water was added in a suitable volume. The paste was granulated, dried, mixed and magnesium stearate, and then compressed, to obtain the tablet.

Such a tablet comprises the following components:

| | |
|---|---|
| Compound of example 1 | 5.0 mg |
| Lactose BP | 150.0 mg |
| Starch BP | 30.0 mg |
| Pregelatinized corn stach BP | 15.0 mg |
| Magnesium stearate | 1.0 mg |

Preparation Example 2

Preparation of Capsule

A capsule containing the cinnamic acid of the present invention as the effective ingredient was prepared as follows.

The compound of example 1 was mixed with a predetermined amount of a vehicle and magnesium state. Thusly obtained mixture was filled in a gelatin capsule.

Such a capsule comprises the following components:

| | |
|---|---|
| Compound of the example 1 | 5.0 mg |
| Starch 1500 | 100.0 mg |
| Magnesium stearate BP | 1.0 mg |

Preparation Example 3

Preparation of Injection

An injection containing the cinnamic acid of the present invention as the effective ingredient was prepared as follows.

The compound of example 1 was dissolved in a suitable volume of saline for injection BP. The pH of the resultant solution was controlled with dilute hydrochloric acid BP to be 3.5, and then the solution volume was controlled with saline for injection BP. The solution was filled in 5 ml type 1 ampule made of transparent glass, and the top of ampule was fused for sealing. The solution contained in the ampule was autoclaved at 120° C. for at least 15 minutes to be sterilized, giving the injection.

Such an injection comprises the following components:

| | |
|---|---|
| Compound of example 1 | 100 µg/ml |
| Dilute hydrochloric acid BP | to be pH 3.5 |
| Saline for injection BP | maximal 1 ml |

Experimental Example 1

Antioxidation Activation Test

1. Preparation of Brain Homogeous Substance

After decapitating a SD rat (male, 10–12 weeks old) and rapidly extracting the brain, 10 mM Tris-HCl buffer solution (pH 7.4) containing 150 mM KCl is added to 10 ml/brain and homogenated. Then, the homogenated brain mixture is centrifuged for 10 minutes at 2,200 rpm, 4° C., and the upper layer is collected through protein assay. The exact amount of protein is measured and kept at −20° C.

2. Lipid Peroxidation Assay

250 µl of brain homogeneous substance (5 mg protein/ml), 10 µl of sample substance, 20 µl of buffer solution is divided at the 96-well micro plate one by one, and cultured for 20 minutes at 37° C. under a shaking condition. Then, 10 µl of 20 µM FeCl2 and 250 µM ascorbic acid is respectively added to the mixture and cultured for 30 minutes at 37° C. After completing the reaction by adding 50 µl of 35% HClO$_4$ to the mixture, the micro plate is centrifuged for 10 minutes at 2,000 rpm, 4° C., and only the upper layer is transferred to the 96-well micro plate in an amount of 240 µl, and then, 120 µl of TBA (thiabarbituric acid; 5 mg/ml in 50% acetic acid) is added to the mixture. After reacting the micro plate for an hour at 80° C., it is cooled at room temperature, and the optical density of the thus obtained TBARS (thiobarbituric acid reactive substances, MDA) is measured at 520 nm.

The assay response curve of TBARS obtained using tetraethoxypropane, a reaction substance of TBA is used in calculating the amount of reaction product MDA of the sample substance, and the oxidation inhibition effect of the test drug is obtained by the following equation 1. Further, the 50% inhibitory concentration (IC$_{50}$) is obtained using the dose response curve.

$$\text{Inhibition ratio (\%)} = \frac{A - B}{A} \times 100 \quad \text{(EQUATION 1)}$$

wherein, A is the concentration (nmol) of the control protein (MDA/mg), and

B is the concentration (nmol) of the experiment protein (MDA/mg).

Therefore, it indicates that the antioxidation activity level is higher when the IC$_{50}$ value is low. The above test results are shown in the following table 4.

TABLE 4

| example | compound | IC$_{50}$ |
|---|---|---|
| 8 | 4-{4-[2-(4-cholrophenyl)-2-hydroethyl]piperazine-1-ylmethyl}-2,6-bis-nonyloxyphenol. | 1.53 µM |
| 12 | 3-(3,5-bis-hexyloxy-4-hydroxyphenyl)-1-[2-{4-fluorophenyl)-2-hydroxyethyl]piperazine-1-yl}propenone | 0.26 µM |

TABLE 4-continued

| example | compound | IC$_{50}$ |
|---|---|---|
| 15 | 1-{4-[2-(4-chlorophenyl)-2-hydroxyethyl]piperazine-1-yl}-3-(3,5-dibutoxy-4-hydroxyphenyl)propan-1-ol | 0.91 μM |
| 16 | N(4-{4-[3-(3,5-di-t-butyl-4-hydroxy-phenyl)-acryloyl]-piperazine-1-yl}-phenyl)-thiophene-2-carboxamidine | 0.51 μM |
| 17 | N[4-(4-{3-[3,5-bis-(1-ethyl-propoxy)-4-hydroxy-phenyl]-acryloyl}-piperazine-1-yl-phenyl]-thiophene-2-carboxamidine | 0.47 μM |
| 18 | N-(4-{4-[3-(4-hydroxy-3,5-dipropoxy-phenyl)-acryloyl]-piperazine-1-yl}-phenyl)-thiophene-2-carboxamidine | 0.49 μM |
| 19 | N-(4-{4-[3-(3,5-dibutoxy-4-hydroxy-phenyl)-acryloyl]-piperazine-1-yl}-phenyl)-thiophene-2-carboxamidine | 038 μM |
| 22 | N-(4-{4-[3-(3,5-dibutoxy-4-hydroxy-phenyl)-acryloyl]-piperazine-1-yl}-phenyl)-1H-pyrrole-2-carboxamidine | 0.37 μM |
| 23 | N-(4-{4-[3-(4-hydroxy-3,5-bis-pentyloxy-phenyl)-acryloyl]-piperazine-1-yl}-phenyl)-1H-pyrrole-2-caroboxamidine | 0.45 μM |
| Comparation | BHT(tert-butyl-hydroxytoluene) | 2.09 μM |

The antioxidation activity level is high when the IC$_{50}$ value is low. As shown in the above table 4, 27% of the antioxidation activity of example 8 of the present invention increased, 88% of the antioxidation activity of example 12 increased, 56% of the antioxidation activity of example 15 increased and 82% of the antioxidation activity of examples 19 and 22 increased compared with the prior antioxidation activator, BHT. Thus, it can be usefully used in treating neurodegerative diseases such as aging, cancer, diabetes, ischemic stroke, Parkinson's disease, dementia, and Huntington's disease.

Experimental Example 2

Acute Toxicity Experiment on Parenteral Administration of Rats

In order to find out whether the compounds of formula 1 and formula 2 have acute toxicity, the following experiment was performed.

A six week old specific pathogen-free (SPF) SD rat was used in the acute toxicity experiment. The compound obtained from examples 1–24 which has been suspended in 0.5% methylcellulose solution was parenterally administered into two rats of each group in the amount of 20 mg/kg/15 ml in one administration.

Then, the present inventors observed the life and death of the animal, clinical symptoms, weight variance, and performed haematological examination and blood-biochemical examination. Further, they observed with the naked eye whether there were any changes at the abdominal organ and thorasic organ after performing necropsy.

As a result, none of the animals administered with the experimental material showed any specific clinical symptoms or death. Further, toxicity change was not observed in weight variance, haematological examination, blood-biochemical examination, necropsy observations and diagnosis, either. From the above results, the compounds used in this experiment are evaluated to be safe substances, since they do not cause any toxic change in rats up to the level of 20 mg/kg, and the oral administration minimum lethal dose (LD$_{50}$) is much higher than 20 mg/kg.

What is claimed is:

1. A compound wherein the compound is selected from the group consisting of:

(1) 4-{4-[2-(4-fluorophenyl)-2-hydroethyl]piperazine-1-ylmethyl-2,6-bis-pentyloxyphenol, (2) 4-{4-[2-(4-chlorophenyl)-2-hydroxyethyl]piperazine-1-ylmethyl}-2,6-bis-nonyloxyphenol, (4) 1-{4-[2-(4-chlorophenyl)-2-hydroxyethyl]piperazine-1-yl}-3-(3,5-dibutoxy-4-hydroxyphenyl)propenone, (5) 3-(3,5-dibutoxy-4-hydroxyphenyl)-1-{4-[2-(4-fluorophenyl)-2-hydroxyethyl]piperazine-1-yl}propenone, (6) 3-(3,5-dibutoxy-4-hydroxyphenyl)-1-[4-(2-hydroxy-2-p-toylethyl)piperazine-1-yl]propenone, (7) 3-(3,5-dibutoxy-4-hydroxyphenyl)-1-{4-[2-hydroxy-2-(4-methoxyphenyl)ethyl]piperazine-1-yl}propenone, (8) 3-(3,5-dibutoxy-4-hydroxyphenyl)-1-{4-[2-hydroxy-2-(3-methoxyphenyl)ethyl]piperazine-1-yl}propenone,

(10) 3-(3,5-bis-hexyloxy-4-hydroxyphenyl)-1-{4-[2-(4-fluorophenyl)-2-hydroxyethyl]piperazine-1-yl}propenone,

(11) 3-[3,5-bis-(1-ethylpropoxy)-4-hydroxyphenyl]-1-{4-[2-(4-chlorophenyl)-2-hydroxyethyl]piperazine-1-yl}propenone,

(12) 1-{4-[2-(4-fluorophenyl)-2-hydroxyethyl]piperazine-1-yl}-3-[4-hydroxy-3,5-bis-nonyloxyphenyl]propenone,

(13) 3-(4-hydroxy-3,5-bis-nonyloxyphenyl)-1-[4-(2-hydroxy-2-p-toylethyl)piperazine-1-yl]propenone,

(14) 3-(4-hydroxy-3,5-bis-nonyloxyphenyl)-1-{4-[2-hydroxy-2-(4-methoxyphenyl)ethyl]piperazine-1-yl}propenone,

(15) 3-(4-hydroxy-3,5-bis-nonyloxyphenyl)-1-{4-[2-hydroxy-2-(3-methoxyphenyl)ethyl]piperazine-1-yl}propenone,

(16) 1-[4-(2-biphenyl-4-yl-2-hydroxyethyl)piperazine-1-yl]-3-(4-hydroxy-3,5-bis-nonyloxyphenyl)propenone, and

(17) 1-{4-[2-(4-chlorophenyl)-2-hydroxyethyl]piperazine-1-yl}-3-(3,5-dibutoxy-4-hydroxyphenyl)propane-1-ol.

2. A pharmaceutical composition, which comprises the compound of claim 1 or a pharmaceutically acceptable salt thereof as an effective ingredient.

* * * * *